US008217178B2

(12) United States Patent
Choi-Sledeski et al.

(10) Patent No.: US 8,217,178 B2
(45) Date of Patent: Jul. 10, 2012

(54) [4-(5-AMINOMETHYL-2-FLUORO-PHENYL)-PIPERIDIN-1-YL]-[7-FLOURO-1-(2-METHOXY-ETHYL)-4-TRIFLUOROM AS AN INHIBITOR OF MAST CELL TRYPTASE

(75) Inventors: Yong Mi Choi-Sledeski, Bridgewater, NJ (US); Nakyen Choy, Bridgewater, NJ (US); Gregory Bernard Poli, Bridgewater, NJ (US); John J. Shay, Jr., Bridgewater, NJ (US); Patrick Wai-Kwok Shum, Bridgewater, NJ (US); Adam W. Sledeski, Bridgewater, NJ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/028,745

(22) Filed: Feb. 16, 2011

(65) Prior Publication Data

US 2011/0201647 A1 Aug. 18, 2011

Related U.S. Application Data

(63) Continuation of application No. PCT/US2009/054381, filed on Aug. 20, 2009.

(60) Provisional application No. 61/091,011, filed on Aug. 22, 2008, provisional application No. 61/091,018, filed on Aug. 22, 2008.

(51) Int. Cl.
*C07D 401/00* (2006.01)
*A61K 31/445* (2006.01)

(52) U.S. Cl. ........................................ 546/201; 514/323

(58) Field of Classification Search ........................ None
See application file for complete search history.

(56) References Cited

U.S. PATENT DOCUMENTS

| | | | |
|---|---|---|---|
| 4,879,119 A | 11/1989 | Konno et al. |
| 4,921,475 A | 5/1990 | Sibalis et al. |
| 4,925,673 A | 5/1990 | Steiner et al. |
| 5,008,110 A | 4/1991 | Benecke et al. |
| 5,013,556 A | 5/1991 | Woodle et al. |
| 5,087,240 A | 2/1992 | Sibalis et al. |
| 5,088,977 A | 2/1992 | Sibalis et al. |
| 5,163,899 A | 11/1992 | Sibalis et al. |
| 5,164,189 A | 11/1992 | Farhadieh et al. |
| 5,254,346 A | 10/1993 | Tucker et al. |
| 5,284,656 A | 2/1994 | Platz et al. |
| 5,290,561 A | 3/1994 | Farhadieh et al. |
| 5,336,168 A | 8/1994 | Sibalis et al. |
| 5,352,456 A | 10/1994 | Fallon et al. |
| 5,407,713 A | 4/1995 | Wilfong et al. |
| 5,451,569 A | 9/1995 | Wong et al. |
| 6,977,263 B2 | 12/2005 | Astles et al. |

FOREIGN PATENT DOCUMENTS

| WO | WO 01/90101 | 11/2001 |
| WO | WO 2005/097780 | 10/2005 |
| WO | WO 2010/022196 A3 | 2/2010 |

OTHER PUBLICATIONS

Seddon "Pseudopolymorph . . . " Crystal growth & design v.4(6) 1087 (2004) (two page from internet).*

Kirk-Othmer "crystallization" Encyclopedia of chem. tech. v. 8, p. 95-147 (2002).*
Braquet, P., et al., Effect of Endothelin-1 on Blood Pressure and Bronchopuimonary System of the Guinea Pig, Journal of Cardiovascular Pharmacology, vol. 13, (Suppl. 5), pp. S143-3146, (1989).
Irani, et al., Human Conjunctival Mast Cells: Distribution of MCT and MCTC in Vernal Conjunctivitis and Giant Papillary Conjunctivitis, Journal of Allergy and Clinical immunology, vol. 86, No. 1, pp. 34-40.
Newmark, J., et al., Preparation and Properties of Adducts of Streptokinase and Streptokinase-Plasmin Complex With Polyethylene Glycol and Pluronic Polyol F38, Journal of Applied Biochemistry, vol. 4, pp. 185-184 (1982).
Wilson, S J., et al., Inflammatory Mediators in Naturally Occurring Rhinitis, Clinical and Experimental Allergy, (1998), vol. 28, pp. 220-227.
Adjei, A., et al., Pulmonary Delivery of Peptide Drugs: Effect of Particle Size on Bioavailability of Leuprolide Acetate in Healthy Male Volunteers, Pharmaceutical Research, vol. 7, No. 6, (1990), pp. 565-569.
Berge, S.M., et al., Pharmaceutical Salts, J. Pharmaceutical Sciences, (1977), vol. 66, No. 1, pp. 1-18.
Buckley, M., et al., Mast Cell Subpopuiations in the Synovial Tissue of Patients with Osteoarthritis: Selective Increase in Numbers of Tryptase-positive, Chymase-negative Mast Cells, Journal of Pathology, vol. 186, (1996) pp. 67-74.
Cairns, J. A., et al., Mast Cell Tryptase Stimulates the Synthesis of Type I Collagenin in Human Lung Fibroblasts, J. Clin. Invest., vol. 99, No. 6, (1997), pp. 1313-1321.

(Continued)

*Primary Examiner* — Janet Andres
*Assistant Examiner* — Heidi Reese
(74) *Attorney, Agent, or Firm* — Ronald G. Ort

(57) ABSTRACT

The present invention is directed to an indole benzylamine compound of formula I:

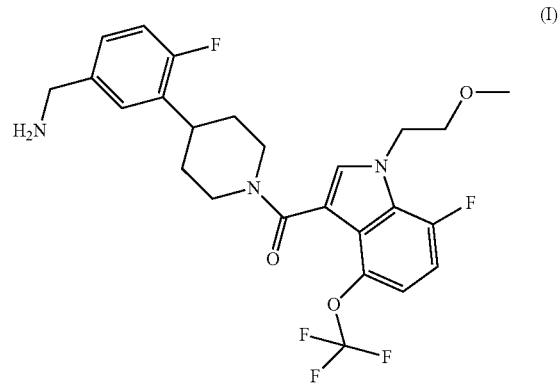

useful as an inhibitor of tryptase. In addition, the present invention is directed to the use of the compound for treating a patient suffering from, or subject to, a physiological condition in need of amelioration by inhibition of tryptase, comprising administering to the patient of a therapeutically effective amount of the compound, and to a pharmaceutical composition comprising a pharmaceutically effective amount of the compound of formula I, and a pharmaceutically acceptable carrier.

9 Claims, 2 Drawing Sheets

OTHER PUBLICATIONS

Caughey, G., et al., Substance P and Vasoactive Intestinal Peptide Degradation by Mast Cell Tryptase and Chymase, The Journal of Pharmacology and Experimental Therapeutics, (1988), vol. 244, No. 1, pp. 133-137.

Debs, R. J., et al., Lung-Specific Delivery of Cytokines Induces Sustained Pulmonary and Systemic Immunodulation in Rats, The Journal of Immunology, vol. 140, pp. 3482-3488, No. 10, (1988).

Franconi, G., et al., Mast Cell Tryptase and Chymase Reverse Airway Smooth Muscle Relaxation induced by Vasoactive Intestinal Peptide in the Ferret, The Journal of Pharmacology and Experimental Therapeutics, (1989), vol. 248, No. 3, pp. 947-951.

Hopkins, C. R., et al., Design, Synthesis, and Biological Activity of Potent and Selective Inhibitors of Mast Cell Tryptase, Bioorganic & Medicinal Chemistry Letters, vol. 15, (2005), pp. 2734-2737.

Jarvikallio, A, et al., Quantitative Analysis of Tryptase- and Chymase-containing Mast Cells in Atopic Dermatitis and Nummular Eczema, British Journal of Dermatology (1997), vol. 136, pp. 871-877.

Jeziorska, M., et al., Mast Cell Distribution, Activation, and Phenotype in Atherosclerotic Lesions of Human Carotid Arteries, Journal of Pathology, vol. 182, 1997, pp. 115-122.

Naukkarinen, A., et al., Immunohistochemical Analysis of Sensory Nerves and Neuropeptides, and Their Contacts with Mast Cells in Developing and Mature Psoriatic Lesions, Archives of Dermatological Research, vol. 285, (1993) pp. 341-346.

Rice, K, et al., Therapeutic Appiications and Design of Mast Cell Tryptase inhibitors, Current Opinion in Drug Discovery and Development, vol. 2, No. 5, pp. 463-474, (1999).

Ruoss, S. j., et al., Mast Cell Tryptase is a Mitogen for Cultured Fibroblasts, J. Clin. Invest., vol. 88, (1991), pp. 493-499.

Schwartz, L., et al., The a Form of Human Tryptase is the Predominant Type Present in Blood at Baseline in Normal Subjects and is Elevated in Those with Systemic Mastocytosis, The Journal of Ciinical investigation, vol. 96, (1995), pp. 2702-2710.

Sekizawa, K., et al., Mast Cell Tryptase Causes Airway Smooth Muscle Hyperresponsiveness in Dogs, J. Clin. Invest., vol. 83, (1989), pp. 175-179.

Sjodin, L., et al., Radioreceptor Assay for Formulation of Salmon Calcitonin, International Journal of Pharmaceutics, vol. 63, (1990), pp. 135-142.

Smith, R M., et al., Pulmonary Deposition and Clearance of Aerosolized Alpha-1-Proteinase Inhibitor Administered to Dogs and to Sheep, J. Clin. Invest., vol. 84, pp. 1145-1154, (1989).

Steinhoff, M., et al., Agonists of Proteinase-activated Receptor 2 Induce Inflammation by a Neurogenic Mechanism, Nature Medicine, vol. 6, No. 2, (2000), pp. 151-158.

Tetlow, L., et al., Distribution, Activation and Tryptase/Chymase Phenotype of Mast Cells in the Rheumatoid Lesion, Annals of the Rheumatic Diseases (1995); vol. 54, pp. 549-555.

Gould, et al., Salt Selection for Basic Drugs, Int'l J Pharmaceutics, (1986), vol. 33, pp. 201-217.

Braquet, P., et al., Effect of Endothelin-1 on Blood Pressure and Bronchopuimonary System of the Guinea Pig, Journal of Cardiovascular Pharmacology, vol. 13, (Suppl. 5), pp. S143-S146, (1989).

Irani, et al., Human Conjunctival Mast Cells: Distribution of MCT and MCTC in Vernal Conjunctivitis and Giant Papillary Conjunctivitis, Journal of Allergy and Clinical Immunology, vol. 86, No. 1, pp. 34-40, 1990.

Hubbard, R. C., et al., Anti-Neutrophil-Elastase Defenses of the Lower Respiratory Tract in a1-Antitrypsin Deficieny Directly Augmented With an Aeroseol of a1-Antitrypsin, Annals of Internal Medicine, vol. 111, No. 3, (1989), pp. 206-212.

Bischoff, S C., et al., Quantitative Assessment of Intestinal Eosinophils and Mast Cells in Inflammatory Bowel Disease, Histopathology, 1996, vol. 28, pp. 1-13.

Zhang, M., et al., Mast Cell Tryptase and Asthma, Mediators of Inflammation, vol. 6, (1997), pp. 311-317.

Tam, et al., Degradation of Airway Neuropeptides by Human Lung Tryptase, Am. J. Respir. Cell Mol. Biol. vol. 3, (1990), pp. 27-32.

Newmark, J., et al., Preparation and Properties of Adducts of Streptokinase and Streptokinase-Plasmin Complex With Polyethylene Glycol and Pluronic Polyol F38, Journal of Applied Biochemistry, vol. 4, pp. 185-189, (1982).

Beil, W. J., et al., Phenotypic and Functional Characterization of Mast Cells Derived from Renal Tumor Tissues, Experimental Hematology, vol. 26, (1998), pp. 158-169.

* cited by examiner

[4-(5-AMINOMETHYL-2-FLUORO-PHENYL)-PIPERIDIN-1-YL]-[7-FLOURO-1-(2-METHOXY-ETHYL)-4-TRIFLUOROM AS AN INHIBITOR OF MAST CELL TRYPTASE

FIELD OF THE INVENTION

This invention is directed to a substituted indole benzylamine compound, its preparation, a pharmaceutical composition comprising the compound, its use, and intermediates thereof.

BACKGROUND OF THE INVENTION

Mast cell mediated inflammatory conditions, in particular asthma, are a growing public health concern. Asthma is frequently characterized by progressive development of hyperresponsiveness of the trachea and bronchi to both immunospecific allergens and generalized chemical or physical stimuli, which lead to the onset of chronic inflammation. Leukocytes containing IgE receptors, notably mast cells and basophils, are present in the epithelium and underlying smooth muscle tissues of bronchi. These leukocytes initially become activated by the binding of specific inhaled antigens to the IgE receptors and then release a number of chemical mediators. For example, degranulation of mast cells leads to the release of proteoglycans, peroxidase, arylsulfatase B, chymase, and tryptase, which results in bronchiole constriction.

Tryptase is stored in the mast cell secretory granules and is the major protease of human mast cells. Tryptase has been implicated in a variety of biological processes, including degradation of vasodilatory and bronchodilatory neuropeptides (Caughey, et al., J. Pharmacol. Exp. Ther., 1988, 244, pages 133-137; Franconi, et al., J. Pharmacol. Exp. Ther., 1988, 248, pages 947-951; and Tam, et al., Am. J. Respir. Cell Mol. Biol., 1990, 3, pages 27-32) and modulation of bronchial responsiveness to histamine (Sekizawa, et al., J. Clin. Invest., 1989, 83, pages 175-179).

As a result, tryptase inhibitors may be useful as anti-inflammatory agents (K Rice, P. A. Sprengler, Current Opinion in Drug Discovery and Development, 1999, 2(5), pages 463-474) particularly in the treatment of chronic asthma (M. Q. Zhang, H. Timmerman, Mediators Inflamm., 1997, 112, pages 311-317), and may also be useful in treating or preventing allergic rhinitis (S. J. Wilson et al, Clin. Exp. Allergy, 1998, 28, pages 220-227), inflammatory bowel disease (S. C. Bischoff et al, Histopathology, 1996, 28, pages 1-13), psoriasis (A. Naukkarinen et al, Arch. Dermatol. Res., 1993, 285, pages 341-346), conjunctivitis (A. A. Irani et al, J. Allergy Clin. Immunol., 1990, 86, pages 34-40), atopic dermatitis (A. Jarvikallio et al, Br. J. Dermatol., 1997, 136, pages 871-877), rheumatoid arthritis (L. C. Tetlow et al, Ann. Rheum. Dis., 1998, 54, pages 549-555), osteoarthritis (M. G. Buckley et al, J. Pathol., 1998, 186, pages 67-74), gouty arthritis, rheumatoid spondylitis, and diseases of joint cartilage destruction.

In addition, tryptase has been shown to be a potent mitogen for fibroblasts, suggesting its involvement in the pulmonary fibrosis in asthma and interstitial lung diseases (Ruoss et al., J. Clin. Invest., 1991, 88, pages 493-499).

Therefore, tryptase inhibitors may be useful in treating or preventing fibrotic conditions (J. A. Cairns and A. F. Walls, J. Clin. Invest., 1997, 99, pages 1313-1321) for example, fibrosis, scleroderma, pulmonary fibrosis, liver cirrhosis, myocardial fibrosis, neurofibromas and hypertrophic scars.

Additionally, tryptase inhibitors may be useful in treating or preventing myocardial infarction, stroke, angina and other consequences of atherosclerotic plaque rupture (M. Jeziorska et al, J. Pathol., 1997, 182, pages 115-122).

Tryptase has also been discovered to activate prostromelysin that in turn activates collagenase, thereby initiating the destruction of cartilage and periodontal connective tissue, respectively.

Therefore, tryptase inhibitors could be useful in the treatment or prevention of arthritis, periodontal disease, diabetic retinopathy, and tumour growth (W. J. Beil et al, Exp. Hematol., (1998) 26, pages 158-169). Also, tryptase inhibitors may be useful in the treatment of anaphylaxis (L. B. Schwarz et al, J. Clin. Invest., 1995, 96, pages 2702-2710), multiple sclerosis (M. Steinhoff et al, Nat. Med. (N. Y.), 2000, 6(2), pages 151-158), peptic ulcers and syncytial viral infections.

Substituted arylmethylamines, represented as by a compound of formula (A), their preparation,

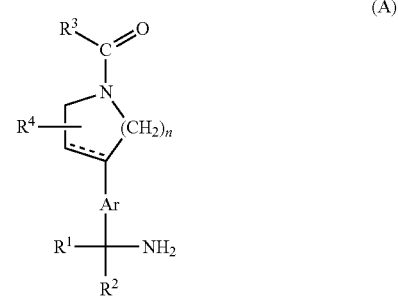

pharmaceutical compositions containing these compounds, and their pharmaceutical use in the treatment of disease states capable of being modulated by the inhibition of tryptase are reported in U.S. Pat. No. 6,977,263. Specifically disclosed in U.S. Pat. No. 6,977,263, are compounds of the following formulae

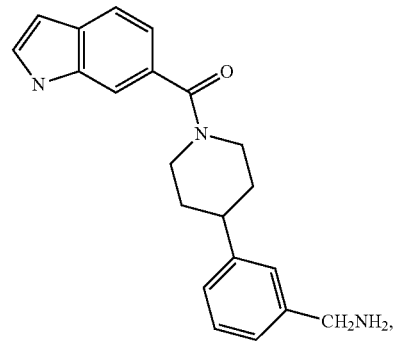

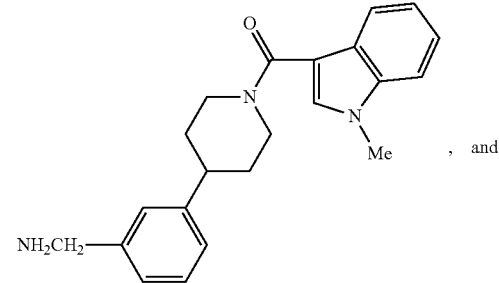

, and

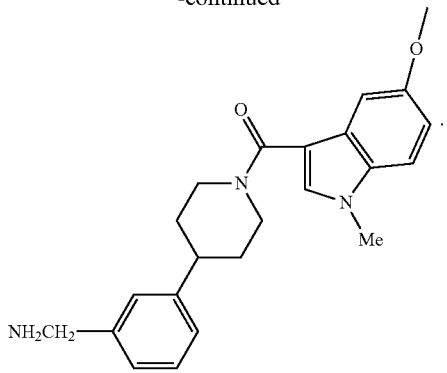

U.S. Pat. No. 6,977,263, however, does not disclose any of the aforesaid [(aminomethyl-phenyl)-piperidin-1-yl]-[indolyl]-methanone species wherein the position para to the aminomethyl group on the phenyl moiety thereof is also substituted with a fluoro group. Furthermore, U.S. Pat. No. 6,977,263, only discloses one [(aminomethyl-phenyl)-piperidin-1-yl]-[indolyl]-methanone compound wherein an aromatic carbon in the indole moiety thereof, other than the one bonded to the carbonyl, is substituted; more specifically solely wherein the 5-position of the indole is substituted by methoxy.

Bioorg. Med. Chem. Lett. 15, 2734 (2005) discloses three types of [(aminomethyl-phenyl)-piperidin-1-yl]-[1H-indoly-3-yl]-methanones as tryptase inhibitors. One type of the inhibitors is directed to a compound of formula B wherein none of the aromatic carbons in the indole moiety

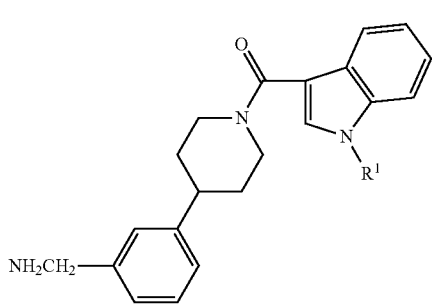

thereof, other than the one bonded to the carbonyl, is substituted, whereas the indole nitrogen is substituted by $R^1$ as hydrogen, methyl, ethyl, isopropyl, propyl, isobutyl, butyl, hexyl, 2-methoxyethyl, cyclohexylmethyl, cyclopropylmethyl, 3-pyridyl, 2-thiazole, acetyl, thiophene-2-carbonyl, benzenesulfonyl, or methanesulfonyl. The second type of the inhibitors is directed to a compound of formula C wherein the indole nitrogen is substituted only by hydrogen and a single aromatic

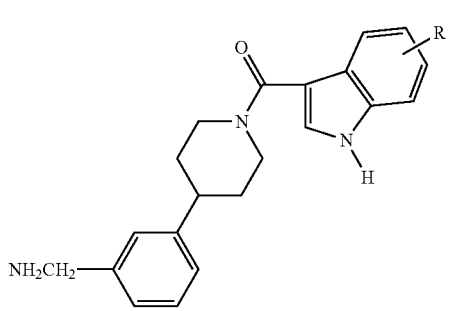

carbon in the indole moiety thereof, other than the one bonded to the carbonyl, is substituted by R as methyl in the 4-, 5-, 6-, or 7-position, or fluoro in the 7-position. The third type of the inhibitors is directed to a compound of formula D wherein a single aromatic carbon in the indole moiety thereof,

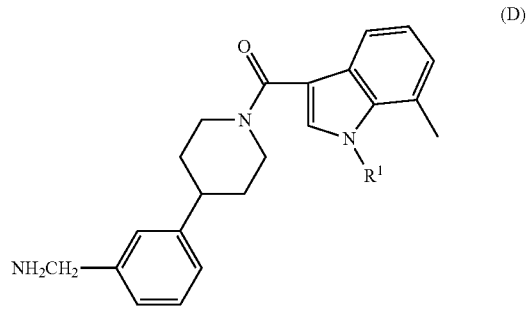

other than the one bonded to the carbonyl, is substituted by methyl in the 7-position, and the indole nitrogen is substituted by $R^1$ as methyl, ethyl, propyl, butyl, or 2-methoxyethyl. Bioorg. Med. Chem. Lett. 15, 2734 (2005) also discloses that substitution on an aromatic carbon in the indole in the 5- or 7-position were tolerated while substitution in the 4- or 6-position gave less active compounds.

No disclosure exists in U.S. Pat. No. 6,977,263 or Bioorg. Med. Chem. Lett. 15, 2734 (2005) of an indole containing tryptase inhibitors wherein: (1) the position para to the aminomethyl group on the phenyl moiety thereof is also substituted with a fluoro group; (2) the indole nitrogen is substituted by 2-methoxyethyl; or (3) two or more aromatic carbons in the indole moiety thereof, other than the one bonded to a carbonyl, are substituted, and that has particularly valuable pharmaceutical properties as a tryptase inhibitor. Such a compound should readily have utility in treating a patient suffering from conditions that can be ameliorated by the administration of an inhibitor of tryptase, e.g., mast cell mediated inflammatory conditions, inflammation, and diseases or disorders related to the degradation of vasodilatory and bronchodilatory neuropeptides, and have diminished liability for semicarbazide-sensitive amine oxidase (SSAO) metabolism.

SUMMARY OF THE INVENTION

Figure 1:
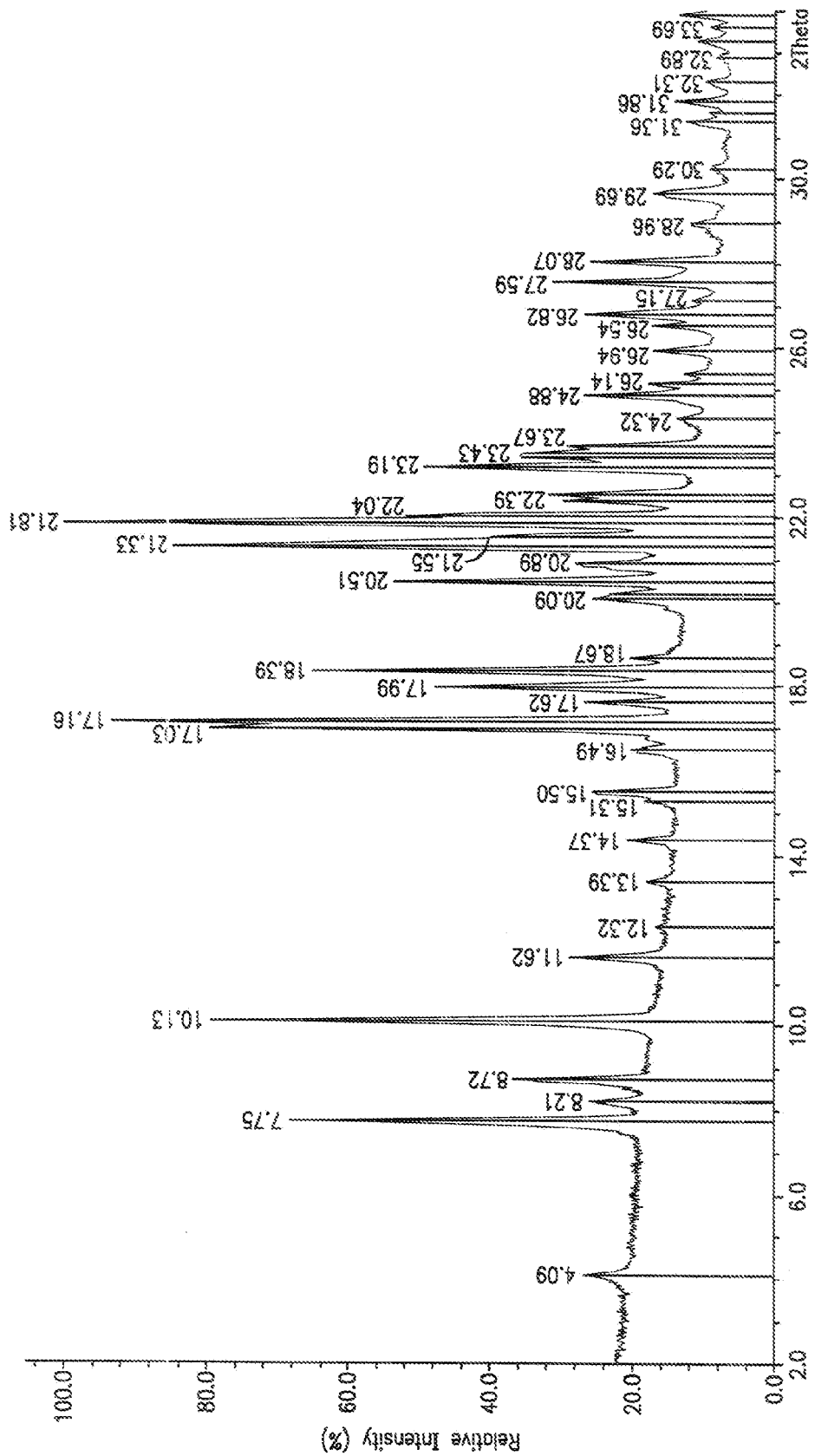
FIG. 1 shows the XRPD results for crystalline form A of the benzoate of the compound of formula I.

The present invention extends to the compound of formula

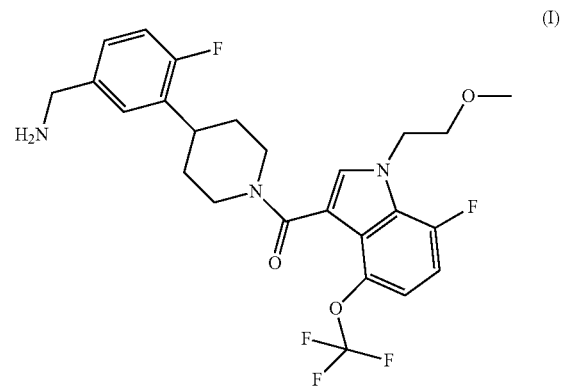

I:

or a prodrug, pharmaceutically acceptable salt, or solvate of said compound.

Furthermore, the present invention is directed to a pharmaceutical composition comprising a pharmaceutically effective amount of the compound of formula I, and a pharmaceutically acceptable carrier.

Furthermore, the present invention is directed to the use of a compound of formula I as an inhibitor of tryptase, comprising introducing the compound into a composition comprising a tryptase inhibitor receptor. In addition, the present invention is directed to the use of a compound of formula I for treating a patient suffering from, or subject to, a physiological condition in need of amelioration with an inhibitor of tryptase comprising administering to the patient a therapeutically effective amount of the compound of claim 1.

The present invention is directed also to the preparation of a compound of formula I, and intermediates useful therein.

Aspects, features and advantages of the present invention will be better understood from the following detailed description, which is given by way of illustration only, and is not limitative of the present invention.

DETAILED DESCRIPTION OF THE INVENTION

List of Abbreviations

As used above, and throughout the description of the invention, the following abbreviations, unless otherwise indicated, shall be understood to have the following meanings:

n-BuOAc n-butyl acetate
n-BuLi n-butyl lithium
sec-BuLi sec-butyl lithium
t-Bu tert-butyl
t-BuOH tert-butanol
CuI copper iodide
DCM dichloromethane, $CH_2Cl_2$ or methylene chloride
DMF dimethylformamide
DMSO dimethylsulfoxide
dppf 1,1'-bis(diphenylphosphino)ferrocene
DSC differential scanning calorimetry
EDCI 1-ethyl-3-(3-dimethylaminopropyl)carbodiimide HCl
eq equivalent(s)
Et ethyl
$Et_2O$ diethyl ether
TEA triethylamine
EtOH ethanol
EtOAc ethyl acetate
EtOC(O)Cl ethyl chloroformate
HPLC high performance liquid chromatography
$MgSO_4$ magnesium sulfate
Me methyl
MeOH methanol
MS mass spectroscopy
MTBE methyl t-butyl ether
$NaHCO_3$ sodium bicarbonate
$Na_2SO_3$ sodium sulfite
$Na_2SO_4$ sodium sulfate
NMR nuclear magnetic resonance
$Pd(PPh_3)_2Cl_2$ bistriphenylphosphine palladium (II) dichloride
$PdCl_2dppf$ 1,1'-bis(diphenylphosphino)ferrocene palladium (II) dichloride
$Pd(dtbpf)Cl_2$ (1,1'Bis(di-t-butylphosphino)ferrocene palladium dichloride
$Pd_2(dba)_3$ tris(dibenzylideneacetone)dipalladium(0)
$Pd(OAc)_2$ palladium(II) acetate
$P(Cy)_3$ tricyclohexylphosphine
$t-Bu_3P$ tri-t-butylphosphine
$PPh_3$ triphenylphosphine
PrOH propanol
iPrOH iso-propanol
i-PrOAc iso-propyl acetate
t-BuOK potassium tert-butoxide
PPSE poly-phosphoric acid trimethylsilylester
$K_2CO_3$ potassium carbonate
$K_2SO_4$ potassium sulfate
LC liquid chromatography
$Na_2SO_4$ Sodium sulfate
rt room temperature
Rt Retention time
TFA trifluoroacetic acid
TFAA trifluoroacetic anhydride
TGA thermogravimetric analysis
THF tetrahydrofuran
TLC thin layer chromatography
TMS-acetylene trimethylsilyl-acetylene Definitions As used above, and throughout the instant specification and appending claims, the following terms, unless otherwise indicated, shall be understood to have the following meanings:

As used herein, the term "compound of the present invention", and equivalent expressions, are meant to embrace the compound of formula I, as hereinbefore described, which expression includes the prodrug, the pharmaceutically acceptable salt and the solvate, e.g., hydrate. Similarly, reference to intermediates, whether or not they themselves are claimed, is meant to embrace the salts, and solvates, where the context so permits. For the sake of clarity, particular instances when the context so permits are sometimes indicated in the text, but these instances are purely illustrative and they are not intended to exclude other instances when the context so permits.

As used herein, the term "treatment" or "treating" includes prophylactic therapy as well as treatment of an established condition, such as for amelioration of the condition of a patient. Such amelioration includes slowing the progression of a disease or a beneficial modification of the condition of the patient.

"Patient" means a human or other mammal.

"Effective amount" is meant to describe an amount of a compound effective in producing the desired therapeutic effect.

"Prodrug" means a compound that is suitable for administration to a patient without undue toxicity, irritation, allergic response, and the like, and is convertible in vivo by metabolic means (e.g. by hydrolysis) to the compound of the present invention. A thorough discussion of prodrugs is provided in T. Higuchi and V. Stella, *Pro-drugs as Novel Delivery Systems*, Vol. 14 of the A. C. S. Symposium Series, and in Edward B. Roche, ed., *Bioreversible Carriers in Drug Design*, American Pharmaceutical Association and Pergamon Press, 1987, both of which are incorporated herein by reference.

"Pharmaceutically acceptable salt" means any salt of these active ingredients with an acid that does not give rise to unwanted toxic or side effects. These acids are well known to pharmacy experts. Non-limiting examples of suitable salts are the following: chloride; bromide; iodide; aspartate, particularly acid aspartate; benzoate, particularly acid benzoate; citrate, particularly acid citrate; tartrate; phosphate, particularly acid phosphate; fumarate, particularly acid fumarate; glycerophosphate; glucose phosphate; lactate; maleate, particularly acid maleate; orotate; oxalate, particularly acid oxalate; sulfate, particularly acid sulfate; trichloroacetate;

trifluoroacetate; besylate; tosylate and methanesulfonate. A list of FDA-approved pharmacologically acceptable salts is given in Philip L. Gould, "Salt Selection for Basic Drugs" 33 Int'l J. Pharm. 201, 202, 214-216 (1986); with further information in Stephen M. Berge et al., "Pharmaceutical Salts", Journal of Pharmaceutical Sciences Vol. 66, No. 1, January 1977, pages 1-19; and methods for making such salts being known in the art from Handbook of Pharmaceutical Salts, P. Heinrich Stahl, Camille G. Wermuth (Eds.), IUPAC Wiley-VCH, 2002; these publications are incorporated herein by reference.

"Solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates, methanolates, and the like.

"Suzuki coupling conditions" mean conditions using a Suzuki coupling solvent, Suzuki coupling catalyst and Suzuki coupling reaction temperature.

"Suzuki coupling solvent" means an alcohol solvent with a boiling point ≧ of isopropyl alcohol, such as n-propyl alcohol, n-butyl alcohol or the like; polar aprotic solvent such as dimethylformamide, 1-methyl-2-pyrrolidone, dimethylsulfoxide, or the like; ethereal solvent such as THF, 2-methylTHF, dimethoxyethane, or the like; or mixture of any of the aforesaid solvents and water or toluene.

"Suzuki coupling catalyst" means a Pd catalyst such as $Pd(PPh_3)_4$, $Pd(PPh_3)_2Cl_2$, $Pd_2(dba)_3$, $Pd(dtbpf)Cl_2$, or the like; or Pd catalyst such as $Pd(OAc)_2$, $Pd_2(dba)_3$ or the like in conjunction with a phosphine ligand such as $PPh_3$, dppf, $t-Bu_3P$, $P(Cy)_3$ or the like.

"Suzuki coupling reaction temperature" means a temperature from about 60° C. to the temperature of the boiling point of the Suzuki coupling reaction mixture.

"trifluoroacetylating conditions" mean conditions using a trifluoroacetylation agent, trifluoroacetylating solvent, and trifluoroacetylation reaction temperature.

"trifluoroacetylation agent" means trifluoroacetic anhydride, 1,1,1-trichloro-3,3,3-trifluoroacetone, trifluoroacetic acid and poly-phosphoric acid trimethylsilylester (PPSE), trifluoroacetyl chloride, trifluoroacetyl fluoride, pentafluorophenyltrifluoroacetate or the like.

"trifluoroacetylating solvent" means a solvent such as an ester solvent such as ethyl acetate, isopropyl acetate, n-butyl acetate or the like; an aromatic hydrocarbon solvent such as toluene, or the like; a chlorinated hydrocarbon solvent such as methylene chloride, 1,2-dichloroethane, or the like.

"trifluoroacetylation reaction temperature" means from about –20 to about 30° C.

"hydrogenation conditions" mean conditions using a hydrogenation catalyst, hydrogenation solvent, hydrogenation reaction temperature, and hydrogenation pressure.

"hydrogenation reaction solvent" means an alcohol solvent such as methanol, ethanol, isopropyl alcohol and the like; or acetic acid; or a mixture of an alcohol solvent or acetic acid and water.

"hydrogenation catalyst" means $PtO_2$, Pd/C, $Pd(OH)_2$, Rh/C and the like, with or without added inorganic acid such as HCl and the like, or organic acid such as acetic acid and the like.

"hydrogenation reaction temperature" means from about 10 to about 60° C.

"hydrogenation pressure" means from about 10 to about 1000 psi of hydrogen (upper limit dictated by equipment capability).

Particular or Preferred Embodiments

In addition, the present invention is directed to the use of the compound of formula I for treating a patient suffering from a physiological condition that can be ameliorated by administering to the patient a therapeutically effective amount of the compound of formula I. Particular embodiments of physiological conditions that can be treated with the compound of the present invention include, but certainly are not limited to inflammatory diseases, e.g., joint inflammation, arthritis, rheumatoid arthritis, rheumatoid spondylitis, gouty arthritis, traumatic arthritis, rubella arthritis, psoriatic arthritis, and other chronic inflammatory joint diseases and asthma and other inflammatory respiratory conditions. Other embodiments of physiological conditions that can be treated by the present invention include physiological conditions such as chronic obstructive pulmonary disease (COPD), COPD exacerbations, joint cartilage destruction, ocular conjunctivitis, vernal conjunctivitis, inflammatory bowel disease, asthma, allergic rhinitis, interstitial lung diseases, fibrosis, scleroderma, pulmonary fibrosis, liver cirrhosis, myocardial fibrosis, neurofibromas, hypertrophic scars, various dermatological conditions, for example, atopic dermatitis and psoriasis, myocardial infarction, stroke, angina and other consequences of atherosclerotic plaque rupture, as well as periodontal disease, diabetic retinopathy, tumour growth, anaphylaxis, multiple sclerosis, peptic ulcers, and syncytial viral infections.

In a particular embodiment, the present invention is directed to the use of a compound of formula I for treating a patient suffering from asthma and other inflammatory respiratory conditions, comprising administering to the patient a physiologically effective amount of the compound.

In another particular embodiment, the present invention is directed to the use of a compound of formula I for treating a patient suffering from COPD, comprising administering to the patient a physiologically effective amount of the compound.

In another particular embodiment, the present invention is directed to the use of a compound of formula I for treating a patient suffering from COPD exacerbations, comprising administering to the patient a physiologically effective amount of the compound.

In another particular embodiment, the present invention is directed to the use of a compound of formula I for treating a patient suffering from allergic rhinitis, comprising administering to the patient a physiologically effective amount of the compound.

In another particular embodiment, the present invention is directed to the use of a compound of formula I for treating a patient suffering from joint inflammation, comprising administering to the patient a physiologically effective amount of the compound.

In another particular embodiment, the present invention is directed to the use of a compound of formula I for treating a patient suffering from inflammatory bowel disease, comprising administering to the patient a physiologically effective amount of the compound.

In addition, the present invention extends to a pharmaceutical composition comprising the compound of formula I, a second compound selected from the group consisting of a beta adrenergic agonist, an anticholinergic, an anti-inflammatory corticosteroid, and an anti-inflammatory agent, and a pharmaceutically acceptable carrier thereof. In such a composition the compound of formula I and the second compound are present in amounts such that provide a therapeutically efficacious activity, i.e., additive or synergistic effect. Particular inflammatory diseases or disorders that can be treated with such a pharmaceutical composition include, but are not limited to, asthma.

Moreover, the present invention is directed to a method for treating a patient suffering from an inflammatory disorder, comprising administering to the patient the compound of formula I and a second compound selected from the group consisting of a beta adrenergic agonist, an anticholinergic, an anti-inflammatory corticosteroid, and an anti-inflammatory agent. In such a method, the compound of formula I and the second compound are present in amounts such that provide a therapeutically efficacious activity, i.e., additive or synergistic effect. In such a method of the present invention, the compound of the present invention can be administered to the patient before a second compound, a second compound can be administered to the patient before a compound of the present invention, or a compound of the present invention and a second compound can be administered concurrently. Particular examples of adrenergic agonists, anticholinergics, anti-inflammatory corticosteroids, and anti-inflammatory agents having application according to the method are described infra. Anticholinergics contemplated for use with the invention include ipratopium bromide and tiotropium. Anti-inflammatory corticosteroids contemplated for use with the invention include beclomethasone dipropionate, triamcinolone acetonide, flunisolide, fluticasone propionate, moetasone furoate, methylprednisone, prednisolone and dexamethasone.

The present invention is also directed to the intermediate compounds of formulae 2-9 for

2

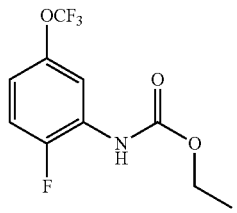

3

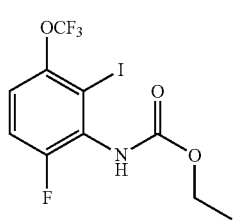

4

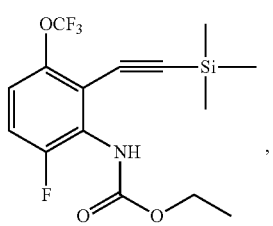

5

6

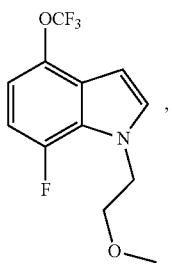

7

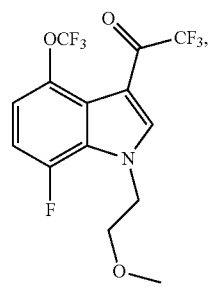

8

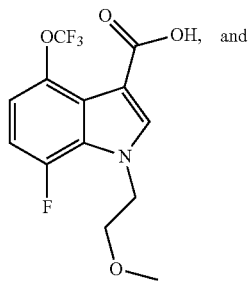

9

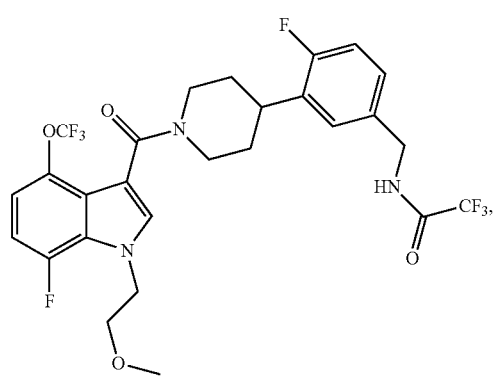

preparing the compound of formula I.

Pharmaceutical Compositions

As explained above, the compound of the present invention exhibits useful pharmacological activity and accordingly may be incorporated into a pharmaceutical composition and used in the treatment of patients suffering from certain medical disorders. The present invention thus provides, according to a further aspect, pharmaceutical compositions comprising the compound of the invention, and a pharmaceutically acceptable carrier thereof. As used herein, the term "pharmaceutically acceptable" preferably means approved by a regulatory agency of a government, in particular the Federal government or a state government, or listed in the U.S. Pharmacopoeia or another generally recognized pharmacopoeia for use in animals, and more particularly in humans. Suitable pharmaceutical carriers are described in "Remington's Pharmaceutical Sciences" by E. W. Martin.

Pharmaceutical compositions according to the present invention can be prepared according to the customary methods, using one or more pharmaceutically acceptable adjuvants or excipients. The adjuvants comprise, inter alia, diluents, fillers, binders, disintegrants, glidants, lubricants, surfactants, sterile aqueous media and the various non-toxic organic solvents. The compositions may be presented in the form of tablets, capsules, pills, sustained release formulations, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, microcrystalline cellulose, pregelatinized starch, unmodified starch, silicified microcrystalline cellulose, mannitol, sorbitol, xylitol, dextrates, fructose, sodium citrate, calcium carbonate, dicalcium phosphate dihydrate, anhydrous dicalcium phosphate, calcium sulfate, along with binders such as polyvinylpyrrolidone, hydroxypropylmethyl cellulose, ethyl cellulose, hydroxyethyl cellulose, methyl cellulose, sodium carboxymethyl cellulose, pregelatinized starch, starch, polyethylene glycols, polyethylene oxide, polycarbophils, gelatin and acacia and disintegrating agents such as sodium croscarmellose, sodium starch glycolate, crospovidone, starch, microcrystalline cellulose, alginic acids and certain complex silicates combined with lubricants such as magnesium stearate, calcium stearate, stearic acid, hydrogenated vegetable oil, mineral oil, polyethylene glycols, glyceryl esters of fatty acids, sodium lauryl sulfate and glidants such as silicon dioxide, talc, starch, along with some suitable wetting agent such as sodium lauryl sulfate, sorbitan esters, polyoxyethylene fatty acid esters, poloxamer, polyoxyethylene ether, sodium docusate, polyethoxylated castor oil, and benzalkonium chloride may be used for preparing tablets. To prepare a capsule, it is advantageous to use fillers such as lactose, microcrystalline cellulose, pregelatinized starch, unmodified starch, silicified microcrystalline cellulose alone or as a mixture of two or more fillers, with and without binders as described above along with suitable wetting agent (s), disintegrants, glidants, lubricants, etc. as listed above. When aqueous suspensions are used they can contain emulsifying agents or agents which facilitate suspension. Diluents such as sucrose, ethanol, polyethylene glycol, propylene glycol, glycerol and chloroform or mixtures thereof may also be used. Such pharmaceutically acceptable carriers can also be sterile water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include mannitol, human serum albumin (HSA), starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like.

Naturally, a pharmaceutical composition of the present invention will contain a therapeutically effective amount of the active compound together with a suitable amount of carrier so as to provide the form for proper administration to the patient. While intravenous injection is a very effective form of administration, other modes can be employed, such as by injection, or by oral, nasal or parenteral administration, which are discussed infra.

Methods of Treatment

The compound of formula I possesses tryptase inhibition activity according to tests described in the literature and described hereinafter, and which test results are believed to correlate to pharmacological activity in humans and other mammals. Thus, in a further embodiment, the present invention is directed to the use of formula I or a composition comprising it for treating a patient suffering from, or subject to, a condition that can be ameliorated by the administration of an inhibitor of tryptase. For example, the compound of formula I is useful for treating an inflammatory disease, for example, joint inflammation, including arthritis, rheumatoid arthritis and other arthritic condition such as rheumatoid spondylitis, gouty arthritis, traumatic arthritis, rubella arthritis, psoriatic arthritis, osteoarthritis or other chronic inflammatory joint disease, or diseases of joint cartilage destruction, ocular conjunctivitis, vernal conjunctivitis, inflammatory bowel disease, asthma, allergic rhinitis, interstitial lung diseases, fibrosis, scleroderma, pulmonary fibrosis, liver cirrhosis, myocardial fibrosis, neurofibromas, hypertrophic scars, various dermatological conditions, for example, atopic dermatitis and psoriasis, myocardial infarction, stroke, angina or other consequences of atherosclerotic plaque rupture, as well as periodontal disease, diabetic retinopathy, tumour growth, anaphylaxis, multiple sclerosis, peptic ulcers, or a syncytial viral infection.

According to a further feature of the invention there is provided a method for the treatment of a human or animal patient suffering from, or subject to, conditions which can be ameliorated by the administration of an inhibitor of tryptase, for example conditions as hereinbefore described, which comprises the administration to the patient of an effective amount of compound of the invention or a composition containing a compound of the invention.

Combination Therapy

As explained above, other pharmaceutically active agents can be employed in combination with the compound of formula I depending upon the disease being treated. For example, in the treatment of asthma, beta-adrenergic agonists such as albuterol, terbutaline, formoterol, fenoterol or prenaline can be included, as can anticholinergics such as ipratropium bromide, anti-inflammatory corticosteroids such as beclomethasone dipropionate, triamcinolone acetonide, flunisolide, fluticasone propionate, mometasone furoate, methylprednisolone, prednisolone, or prednisone; and anti-inflammatory agents such as sodium cromoglycate and nedocromil sodium. Thus, the present invention extends to a pharmaceutical composition comprising the compound of formula I and a second compound selected from the group consisting of a beta adrenergic agonist, an anticholinergic, an anti-inflammatory corticosteroid, a leukotriene receptor antagonist, a lipoxygenase inhibitor, a phosphodiesterase-4 inhibitor, and an anti-inflammatory agent; and a pharmaceutically acceptable carrier thereof. Particularly contemplated for use with the present invention as a leukotriene antagonist is montelukast. And Particularly contemplated for use with the present invention as phosphodiesterase-4 inhibitors are roflumilast and ciflumilast. Particular pharmaceutical carriers having applications in this pharmaceutical composition are described herein.

Furthermore, the present invention extends to a method for treating a patient suffering from asthma, comprising administering the patient the compound of the present invention, and a second compound selected from the group consisting of a beta adrenergic agonist, an anticholinergic, an anti-inflammatory corticosteroid, a leukotriene receptor antagonist, a lipoxygenase inhibitor, a phosphodiesterase-4 inhibitor, and an anti-inflammatory agent. In such a combination method, the compound of the present invention can be administered prior to the administration of the second compound, the compound of the present invention can be administered after administration of the second compound, or the compound of the present invention and the second compound can be administered concurrently.

Modes of Delivery

According to the invention, the compound of formula I, or a pharmaceutical composition comprising the compound, may be introduced parenterally, transmucosally, e.g., orally, nasally, pulmonarily, or rectally, or transdermally to a patient.

Oral Delivery

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for a therapeutic is given by Marshall, K. In: *Modern Pharmaceutics* Edited by G. S. Banker and C. T. Rhodes Chapter 10, 1979, herein incorporated by reference. In general, the formulation will include a compound of the present invention, and inert ingredients that allow for protection against the stomach environment, and release of the biologically active material, i.e., a compound of the present invention, in the intestine.

Also specifically contemplated are oral dosage forms of the compound of the present invention. Such a compound may be chemically modified so that oral delivery is more efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the compound of the present invention, and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, NY, pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the compound of the present invention, the location of release may be the stomach, the small intestine (the duodenum, the jejunum, or the ileum), or the large intestine. One skilled in the art has available formulations that will not dissolve in the stomach, yet will release the material in the duodenum or elsewhere in the intestine. Preferably, the release will avoid the deleterious effects of the stomach environment, either by protection of the compound of the present invention, or by release of the compound beyond the stomach environment, such as in the intestine.

To ensure full gastric resistance a coating impermeable to at least pH 5 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings that make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the present invention may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicel.

Disintegrants may be included in the formulation of the therapeutic into a solid dosage form. Materials used as disintegrates include, but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential non-ionic detergents that could be included in the formulation as surfactants are Lauromacrogol 400, Polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of a compound of the present invention either alone or as a mixture in different ratios.

Additives that potentially enhance uptake of the compound of the present invention are, for instance, the fatty acids oleic acid, linoleic acid and linolenic acid. Controlled release oral formulation may be desirable. The drug could be incorporated into an inert matrix that permits release by either diffusion or leaching mechanisms, e.g., gums. Slowly degenerating matrices may also be incorporated into the formulation. Some enteric coatings also have a delayed release effect.

Another form of a controlled release of this therapeutic is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars that could be applied in a coating pan. The therapeutic agent could also be given in a film-coated tablet and the materials used in this instance are divided into 2 groups. The first are the non-enteric materials and include methyl cellulose, ethyl cellulose, hydroxyethyl cellulose, methylhydroxyethyl cellulose, hydroxypropyl cellulose, hydroxypropyl-methyl cellulose, sodium carboxymethyl cellulose, povidone and the polyethylene glycols. The second group consists of the enteric materials that are commonly esters of phthalic acid.

A mix of materials might be used to provide the optimum film coating. Film coating may be carried out in a pan-coater or in a fluidized bed or by compression coating.

Pulmonary Delivery

Also contemplated herein is pulmonary delivery of the compound of the present invention, either alone, or in a pharmaceutical composition. The compound is delivered to the lungs of a mammal while inhaling and traverses across the lung epithelial lining to the blood stream. Other reports of this include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, J. Immunol. 140:3482-3488 (interferon-γ and tumour necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Col.; the Ventolin metered dose inhaler, manufactured by Glaxo Inc., Research Triangle Park, N.C.; and the Spinhaler powder inhaler, manufactured by Fisons Corp., Bedford, Mass., to name only a few.

All such devices require the use of formulations suitable for the dispensing of the compound of the present invention. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. A chemically modified compound of the present invention may also be prepared in different formulations depending on the type of chemical modification or the type of device employed.

Formulations suitable for use with a nebulizer, either jet or ultrasonic, will typically comprise the compound of the present invention dissolved in water at a concentration of about 0.1 to 25 mg of compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the compound of the invention suspended in a propellant with the aid of a surfactant. The propellant may be any conventional material employed for this purpose, such as a chlorofluorocarbon, hydrochlorofluorocarbon, hydrofluorocarbon, or hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the compound of the invention, and may also include a bulking agent, such as lactose, sorbitol, sucrose, or mannitol in amounts which facilitate dispersal of the powder from the device, e.g., 50 to 90% by weight of the formulation. The compound of the present invention should most advantageously be prepared in particulate form with an average particle size of less than 10 mm (or microns), most preferably 0.5 to 5 mm, for most effective delivery to the distal lung.

Nasal Delivery

Nasal delivery of the compound of the present invention is also contemplated. Nasal delivery allows the passage of the compound to the blood stream directly after administering the therapeutic product to the nose, without the necessity for deposition of the product in the lung. Formulations for nasal delivery include those with dextran or cyclodextran.

Transdermal Delivery

Various and numerous methods are known in the art for transdermal administration of a drug, e.g., via a transdermal patch, have applications in the present invention. Transdermal patches are described in for example, U.S. Pat. Nos. 5,407,713, 5,352,456, 5,332,213, 5,336,168, 5,290,561, 5,254,346, 5,164,189, 5,163,899, 5,088,977, 5,087,240, 5,008,110, and 4,921,475, the disclosure of each of which is incorporated herein by reference in its entirety.

It can be readily appreciated that a transdermal route of administration may be enhanced by use of a dermal penetration enhancer, e.g., such as enhancers described in U.S. Pat. Nos. 5,164,189, 5,008,110, and, 4,879,119, the disclosure of each of which is incorporated herein by reference in its entirety.

Topical Administration

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

Rectal Administration

Solid compositions for rectal administration include suppositories formulated in accordance with known methods and containing the compound of the invention.

Dosages

The percentage of active ingredient in the composition of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

Furthermore, the compound according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Naturally, a patient in whom administration of the compound of the present invention is an effective therapeutic regimen is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Preparatory Details

The compound of formula I may be prepared by the application or adaptation of known methods, by which is meant methods used heretofore or described in the literature, for example those described by R. C. Larock in Comprehensive Organic Transformations, VCH publishers, 1989, or as described herein.

In the reactions described hereinafter it may be necessary to protect reactive functional groups, for example, amino groups, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

In particular, the compound of formula I may be prepared as shown through Schemes 1-2.

For example, the compound of the present invention is an achiral compound whose preparation is comprised of a convergent synthesis. The compound of the invention, as its benzoate salt, is prepared as shown in the schemes below.

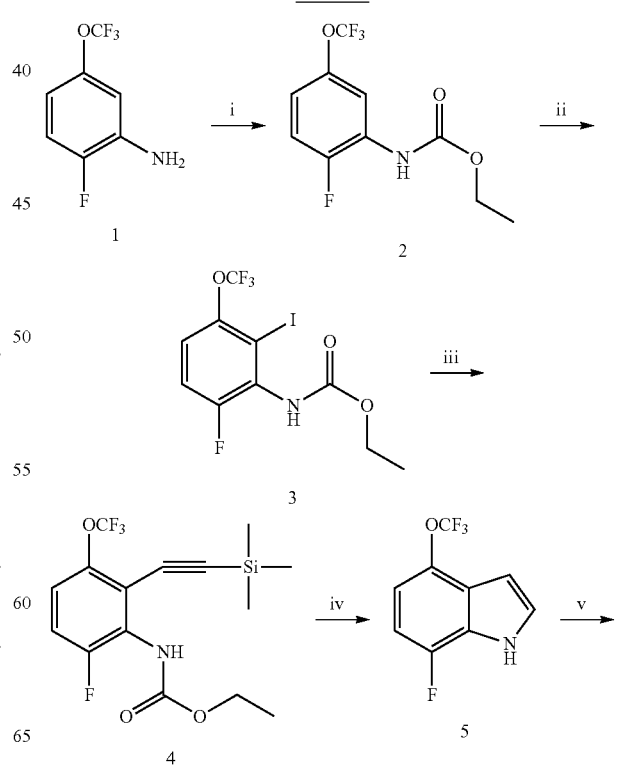

Scheme 1

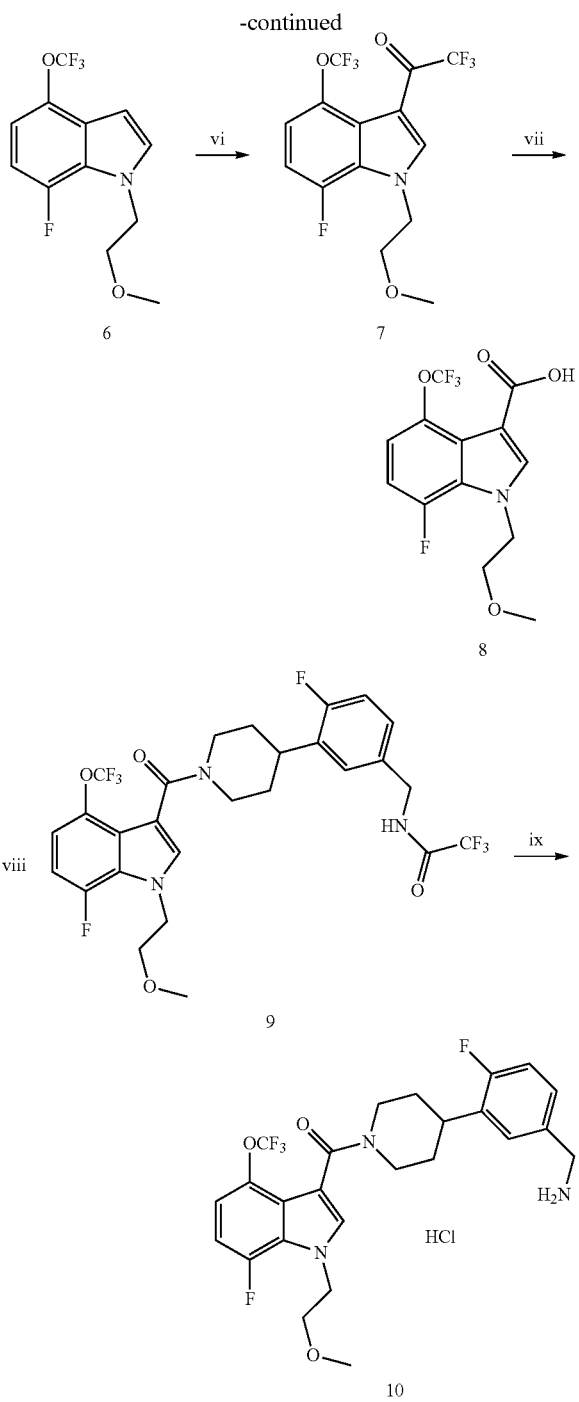

(i) Ethyl chloroformate, pyridine, THF, 0° C., 100%;
(ii) a: sec-BuLi, THF, -78° C., b; I₂, THF, -78° C., 52-68%;
(iii) TMS-acetylene, TEA, CuI, Pd(PPh₃)₂Cl₂, degassed THF, 60° C., 93%; (iv) KOH, t-BuOH, 70° C., 91%;
(v) Powder KOH, 2-methoxyethyl bromide, DMSO, rt, 95%;
(vi) TFAA, DMF, 40° C., 89%;
(vii) 5M NaOH, MeOH, 85° C., 96%;
(viii) 2,2,2-Trifluoro-N-(fluoro-3-piperidin-4-yl-benzyl)-acetamide hydrochloride, EDCI, TEA, CH₂Cl₂ (DCM), rt, 99%;
(ix) a: K₂CO₃, MeOH/H₂O, b: 1M HCl in Et₂O, 90%

Compound 1 is converted to compound 2 by protecting the amino group with an amino protecting agent, such as ethyl chloroformate in the presence of a suitable base, such as pyridine, to yield protected compound 2.

Compound 2 is converted to compound 5 in a three step process. Compound 2 is iodinated in the position next to the carbamic ester by reacting 2 with a strong base such as secondary butyl lithium to form the anion which is reacted with an iodide source such as molecular iodine to give compound 3. Compound 3 is then converted to acetylenic compound 4 using catalytic conditions such as copper (I) iodide and bistriphenylphosphine palladium (II) dichloride in the presence of trimethylsilylacetylene and base such as triethylamine. Compound 4 is cyclized using a strong base such as potassium hydroxide and heating to give indole compound 5.

Compound 5 is converted to compound 6 by alkylating the indole nitrogen thereof with an alkyl halide in the presence of a strong base, such as a potassium hydroxide, in a dipolar aprotic solvent, such as dimethylsulfoxide, at room temperature to yield compound 6.

Compound 6 is converted to compound 8 in a two step process. First, compound 6 is converted to compound 7 by treating compound 6 with trifluoroacetic anhydride in the presence of a solvent such as N,N-dimethylformamide and heating. Compound 7 is treated with a strong base such as sodium hydroxide to give compound 8 which has an acid function in the 3-position thereof.

Compound 8 is converted to amide 9 by reacting acid 8 with 2,2,2-trifluoro-N-(fluoro-3-piperidin-4-yl-benzyl)-acetamide hydrochloride (compound 14) in the presence of an acid coupling reagent such as EDCI and an organic base such as triethylamine in an inert solvent such as dichloromethane.

Compound 9 is converted to compound 10 by deprotecting N-benzyl trifluoroacetamide on treatment with mild base, such as potassium carbonate, in solvent mixture, such as methanol/water. The hydrochloride salt can be formed in the presence of a polar organic solvent, such as ether, to yield compound 10 which is the hydrochloride salt of ([4-(5-aminomethyl-2-fluoro-phenyl)-piperidin-1-yl]-[7-fluoro-1-(2-methoxy-ethyl)-4-methyl-1H-indol-3-yl]-methanone) in formula I.

The reactions of this scheme are as follows.

Step A: Preparation of
(2-Fluoro-5-trifluoromethoxy-phenyl)-carbamic acid ethyl ester (2)

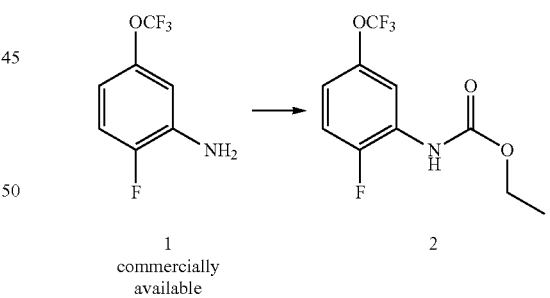

1
commercially available

2

To a solution of 1 (50.72 g, 0.26 mol) and pyridine (27.3 mL, 0.34 mol) in THF (500 mL) at 0° C. is added ethyl chloroformate (32.2 mL, 0.39 mol) dropwise over a 30 min period. After 1 h, both LC/MS and TLC indicate that the reaction is completed. The reaction mixture is partitioned between H₂O and EtOAc. The two layers are separated, and the organic layer is washed with 1 M HCl, H₂O, and brine, dried over MgSO₄, filtered, and concentrated in vacuo. The crude material is purified on silica gel with heptane/EtOAc (95/5 to 70/30) as eluant to give 69.23 g (99%) of the product 2 as a clear colorless liquid. ¹H NMR (CDCl₃) δ 8.11 (br s, 1H), 7.07 (dd, J=9.1, 9.3 Hz, 1H), 7.00-6.80 (m, 2H), 4.27 (q, J=7.1 Hz, 2H), 1.33 (t, J=7.1 Hz, 3H); $^{19}$F NMR (CDCl$_3$) δ −57.84 (s, 3F), −134.01 (br s, 1F); MS 309 (M+CH3CN+1, 100%), 268 (M+1).

Step B: Preparation of (6-Fluoro-2-iodo-3-trifluoromethoxy-phenyl)-carbamic acid ethyl ester (3)

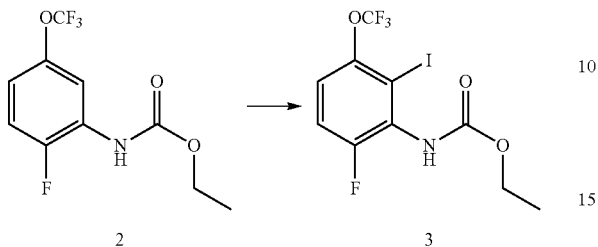

To a solution of 2 (31.34 g, 117.2 mmol) in THF (180 mL) at −78° C. is added sec-BuLi (1.4 M in cyclohexane, 200 mL, 280 mmol) dropwise over a 1 h period. After 20 min, a solution of I$_2$ (44.6 g, 175.8 mmol) in THF (150 mL) is added dropwise over a 30 min period. This mixture is then stirred at −78° C. for 30 min. Saturated NH$_4$Cl is added, and the cooling bath is removed. The reaction mixture is partitioned between H$_2$O and EtOAc. The two layers are separated, and the organic layer is washed with 10% Na$_2$SO$_3$, H$_2$O, and brine, dried over MgSO$_4$, filtered, and concentrated in vacuo. The residue is suspended in DCM (50 mL), and heptane (300 mL) is added. The white powder 3 (18.1 g, 39%) from the resulting suspension is collected by suction filtration and air-dried. The filtrate is concentrated in vacuo, and the residue is suspended in heptane (200 mL). Another batch of 3 (3.8 g, 8%) is collected by suction filtration and air-dried. Additional product can be obtained by purifying the filtrate via silica gel chromatography. $^1$H NMR (CDCl$_3$) δ 7.30-17.10 (m, 2H), 6.16 (br s, 1H), 4.26 (q, J=7.1 Hz, 2H), 1.32 (t, J=7.1 Hz, 3H); $^{19}$F NMR (CDCl$_3$) δ −56.90 (s, 3F), −114.35 (d, J=8.5 Hz, 1F); MS 394 (M+1, 100%), 374, 364, 321, 267.

Step C: Preparation of (6-Fluoro-3-trifluoromethoxy-2-trimethylsilanylethynyl-phenyl)-carbamic acid ethyl ester (4)

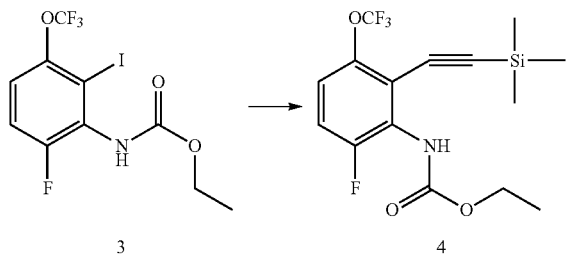

A mixture of 3 (18.1 g, 45.9 mmol), Et$_3$N (12.8 mL, 91.9 mmol), Pd(PPh)$_2$Cl$_2$ (1.6 g, 5% mol), CuI (0.7 g, 8% mol), and TMS-acetylene (19.6 mL, 137.8 mmol) in degassed THF (180 mL) is heated at 60° C. overnight. The mixture is cooled to rt, and then partitioned between H$_2$O and EtOAc. This mixture is filtered through Celite to remove the insoluble material. The two layers of the filtrate are separated, and the organic layer is washed H$_2$O and brine, dried over MgSO$_4$, filtered, and concentrated in vacuo. The crude material is purified on silica gel with heptane/EtOAc as eluant to give 15.6 g (93%) of the product 4 as beige solid. $^1$H NMR (CDCl$_3$) δ 7.15-7.00 (m, 2H), 6.41 (br s, 1H), 4.26 (q, J=7.1 Hz, 2H), 1.31 (t, J=7.1 Hz, 3H), 0.27 (s, 9H); $^{19}$F NMR (CDCl$_3$) δ −57.59 (s, 3F), −118.15 (s, 1F); MS 364 (M+1, 100%).

Step D: Preparation of 7-Fluoro-4-trifluoromethoxy-1H-indole (5)

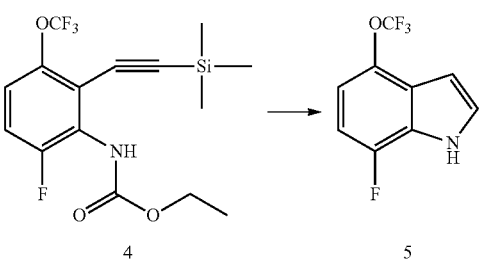

A mixture of 4 (28.9 g, 79.6 mmol) and KOH (35.7 g, 636.7 mmol) in degassed t-BuOH (300 mL) is heated at 70° C. overnight. LC/MS indicates the reaction is completed. The mixture is cooled to rt, and then partitioned between H$_2$O and Et$_2$O. The two layers are separated, and the aqueous layer was extracted with Et$_2$O (2×). The combined organic layers are washed with H$_2$O and brine, dried over MgSO$_4$, filtered, and concentrated in vacuo. The crude material is purified on silica gel with heptane/EtOAc (100/0 to 60/40) as eluant to give 16 g (91%) of 5 as a yellow liquid. $^1$H NMR (CDCl$_3$) δ 8.47 (br s, 1H), 7.35-7.20 (m, 1H), 6.95-6.80 (m, 2H), 6.68 (d, J=2.5 Hz, 1H); $^{19}$F NMR (CDCl3) δ −57.63 (s, 3F), −136.10 (d, J=8.5 Hz, 1F); MS 220 (M+1, 100%), 200.

Step E: Preparation of 7-Fluoro-1-(2-methoxyethyl)-4-trifluoromethoxy-1H-indole (6)

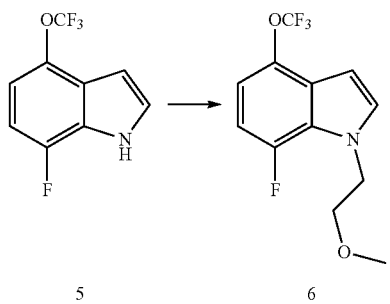

A mixture of 5 (16 g, 72.8 mmol) and powder KOH (20.4 g, 364.2 mmol) in DMSO (150 mL) is stirred at rt for 10 min. 2- Methoxyethyl bromide (10.3 mL, 109.2 mmol) is added. This mixture is stirred at rt overnight. LC/MS indicates the reaction is completed. The mixture is partitioned between H$_2$O and Et$_2$O. The two layers are separated, and the aqueous layer is extracted with Et$_2$O (2×). The combined organic layers are washed with H$_2$O and brine, dried over MgSO$_4$, filtered, and concentrated in vacuo. The crude material is purified on silica gel with heptane/EtOAc (100/0 to 50/50) as eluant to give 19.3 g (95%) of 6 as a yellow liquid. $^1$H NMR (CDCl$_3$) δ 7.15 (d, J=2.1 Hz, 1H), 6.90-6.75 (m, 2H), 6.56 (t, J=2.5 Hz, 1H), 3.72 (t, J=5.2 Hz, 2H), 3.72 (t, J=5.2 Hz, 2H), 3.31 (s, 3H); $^{19}$F NMR (CDCl$_3$) δ −57.54 (s, 3F), −137.00 (d, J=11.3 Hz, 1F); MS 278 (M+1, 100%).

Step F: Preparation of 2,2,2-Trifluoro-1-[7-fluoro-1-(2-methoxy-ethyl)-4-trifluoromethoxy-1H-indol-3-yl]-ethanone (7)

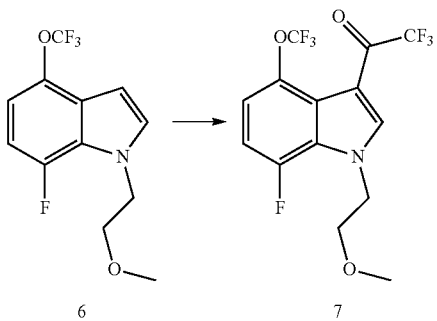

To a mixture of 6 (19.3 g, 69.7 mmol) in DMF (135 mL) is added TFAA (26.2 mL, 188.2 mmol). This mixture is heated at 40° C. overnight. TLC indicates the reaction is completed. The mixture is cooled to rt, and then partitioned between $H_2O$ and $Et_2O$. The two layers are separated, and the organic layer is washed with saturated $NaHCO_3$ (2×), $H_2O$ and brine, dried over $MgSO_4$, filtered, and concentrated in vacuo. The crude material is purified on silica gel with heptane/EtOAc (100/0 to 50/50) as eluant to give 23.4 g (89%) of 7 as a slightly green solid. $^1H$ NMR (CDCl$_3$) δ 8.03 (d, J=1.4 Hz, 1H), 7.20-6.95 (m, 2H), 4.54 (t, J=4.9 Hz, 2H), 3.76 (t, J=4.8 Hz, 2H), 3.33 (s, 3H); $^{19}F$ NMR (CDCl$_3$) δ −57.74 (s, 3F), −71.10 (s, 3F), −134.95 (d, J=11.5 Hz, 1F); MS 374 (M+1, 100%).

Step G: Preparation of 7-Fluoro-1-(2-methoxy-ethyl)-4-trifluoromethoxy-1H-indole-3-carboxylic acid (8)

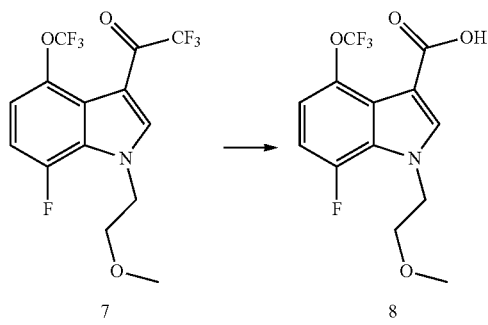

A mixture of 7 (23.4 g, 62.6 mmol) in MeOH (100 mL) and 5 M NaOH (100 mL) is heated at 80° C. overnight. LC/MS indicates that the reaction is complete. The reaction mixture is cooled to rt, and then concentrated in vacuo to remove most of the MeOH. The residue is dissolved in $H_2O$, and then washed with $Et_2O$ once. The aqueous layer is slowly acidified to pH~2 with conc. HCl. The acidified suspension is extracted with $Et_2O$, and the organic extract is washed with $H_2O$ and brine, dried over $MgSO_4$, filtered, and concentrated in vacuo. The residue is suspended in DCM/heptane (10/90). The white powder 8 (19.4 g, 96%) in the suspension is collected by suction filtration and air-dried. $^1H$ NMR (CDCl$_3$) δ 8.02 (s, 1H), 7.15-7.05 (m, 1H), 7.00-6.90 (m, 1H), 4.49 (t, J=5.0 Hz, 2H), 3.75 (t, J=4.9 Hz, 2H), 3.33 (s, 3H); $^{19}F$ NMR (CDCl$_3$) δ −57.74 (s, 3F), −135.65 (d, J=11.3 Hz, 1F); MS 363 (M+CH$_3$CN+1, 100%).

Step H: Preparation of 2,2,2-Trifluoro-N-(4-fluoro-3-{1-[7-fluoro-1-(2-methoxy-ethyl)-4-trifluoromethoxy-1H-indole-3-carbonyl]piperidin-4-yl}-benzyl)-acetamide (9)

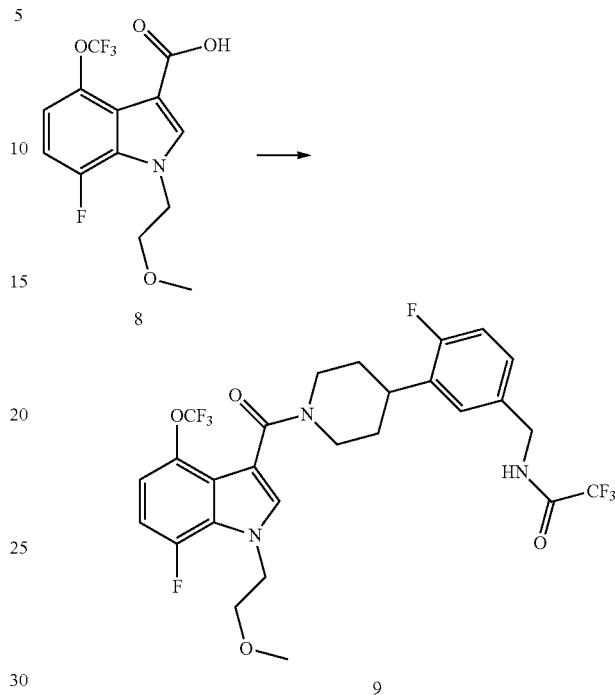

A mixture of 8 (19.1 g, 59.6 mmol), Et$_3$N (24.8 mL, 177.9 mmol), 2,2,2-trifluoro-N-(4-fluoro-3-piperidin-4-yl-benzyl)-acetamide hydrochloride (11, 26.4 g, 77.5 mmol) (14), and EDCI (17.1 g, 89.3 mmol) in CH$_2$Cl$_2$ is stirred at rt overnight. Both TLC and LC/MS indicate that the reaction is completed. The mixture is partitioned between $H_2O$ and CH$_2$Cl$_2$. The two layers are separated, and the organic layer is washed with brine, dried over $MgSO_4$, filtered, and concentrated in vacuo. The crude material is purified on silica gel with heptane/EtOAc (40/60 to 0/100) as eluant to give 9 (36 g, 99%) as a white foam. $^1H$ NMR (CDCl$_3$) δ 7.37 (s, 1H), 7.20-7.10 (m, 2H), 7.10-6.85 (m, 4H), 4.95 (br s, 1H), 4.60-4.35 (m, 4H), 3.90 (br s, 1H), 3.73 (t, J=5.0 Hz, 2H), 3.32 (s, 3H), 3.25-2.70 (m, 3H), 2.05-1.50 (m, 4H); $^{19}F$ NMR (CDCl$_3$) δ −57.54 (s, 3F), −75.39 (s, 3F), −119.31 (s, 1F), −134.96 (d, J=11.3 Hz, 1F); MS 608 (M+1, 100%).

Step I: Preparation of [4-(5-Aminomethyl-2-fluoro-phenyl)-piperidin-1-yl]-[7-fluoro-1-(2-methoxy-ethyl)-4-trifluoromethoxy-1H-indol-3-yl]-methanone hydrochloride salt (10)

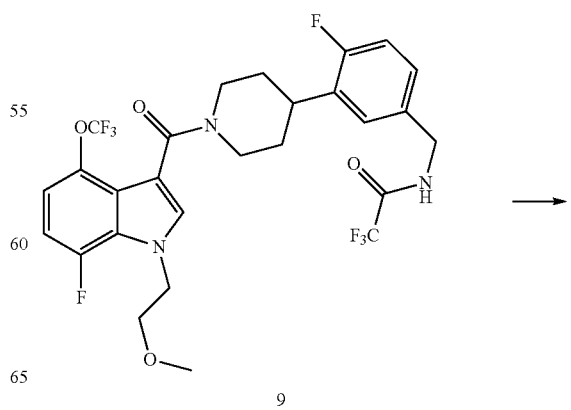

-continued

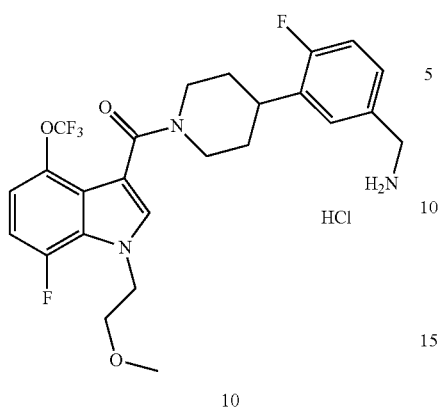

10

To a mixture of 9 (36 g, 59.3 mmol) in MeOH (400 mL) is added aqueous K₂CO₃ (65.5 g, 474 mmol, dissolved in 120 mL H₂O). This mixture is stirred at rt overnight. LC/MS indicates the reaction is completed. The reaction mixture is concentrated in vacuo to remove most of the methanol. The residue is partitioned between H₂O and EtOAc. The two layers are separated, and the organic layer is washed with H₂O and brine, dried over MgSO₄, filtered, and concentrated in vacuo to yield 27.5 g (90%) of 10 as a clear colorless sticky gum.

$^1$H NMR (CDCl₃) δ 7.42 (s, 1H), 7.25-7.10 (m, 2H), 7.05-6.85 (m, 3H), 4.92 (br s, 1H), 4.46 (t, J=5.2 Hz, 2H), 3.86 (br s, 3H), 3.74 (t, J=5.1 Hz, 2H), 3.32 (s, 3H), 3.30-2.75 (m, 3H), 2.24 (br s, 2H), 2.05-1.55 (m, 4H); $^{19}$F NMR (CDCl₃) δ −57.52 (s, 3F), −121.64 (s, 1F), −136.03 (d, J=11.3 Hz, 1F); MS 512 (M+1, 100%).

To a solution of the above material (2.856 g, 5.59 mmol) in Et₂O (30 mL) is added 2 N HCl/Et₂O (3 mL, 6 mmol) dropwise. A solid precipitate forms and the ethereal solution is decanted off. The solid is washed with additional Et₂O then decanted off. The remaining pale yellow solid is dissolved in warm MeOH (10 mL) then Et₂O (50 mL) is added until the solution is slightly cloudy. After ca. 2 hrs solid precipitate appears. Additional Et₂O (5-10 mL) is added and then the suspension is placed in the fridge overnight. A white crystalline product (2.475 g, 4.52 mmol) is collected and dried under high vacuum for 4 hrs.

$^1$H NMR (DMSO-d₆) δ 8.32 (br s, 2H), 7.71 (s, 1H), 7.43 (d, 1H, J=7.2 Hz), 7.36 (m, 1H), 7.26-7.20 (m, 1H), 7.12-7.08 (m, 2H), 4.49 (t, J=5.1Hz, 2H), 4.00 (s, 2H), 3.71 (t, J=5.1 Hz, 2H), 3.32 (s, 3H), 3.21-3.07 (m, 3H), 2.99 (br s, 2H), 1.80-1.62 (m, 4H); $^{19}$F NMR (DMSO-d₆) δ −56.79 (s, 3F), −119.34 (s, 1F), −134.53 (d, J=9.6 Hz, 1F); MS 512 (M+1, 100%). CHN:

Theoretical: C, 53.06%, H, 5.16%, N, 7.42% (calc'd as 1.0 H₂O). Found: C, 53.03%, H, 4.82%, N, 7.22; Cl, 6.64%.

[4-(5-Aminomethyl-2-fluorophenyl)piperidine-1-yl]
[7-fluoro-1-(2-methoxyethyl)-4-trifluoromethoxy-
1H-indol-3-yl]methanone Benzoate
(10 benzoate salt).

A 20-L glass-jacketed reactor already containing a toluene solution assumed to contain [4-(5-aminomethyl-2-fluorophenyl)piperidine-1-yl][7-fluoro-1-(2-methoxyethyl)-4-trifluoromethoxy-1H-indol-3-yl]methanone (1320 g, 2.58 mol) is stirred and heated to 61° C. Benzoic acid (316 g, 2.58 mol) is added and, after all the benzoic acid has dissolved, cyclohexane (6.04 L) is added. The reaction is heated to 77° C. where it is seeded with [4-(5-aminomethyl-2-fluorophenyl)piperidine-1-yl][7-fluoro-1-(2-methoxyethyl)-4-trifluoromethoxy-1H-indol-3-yl]methanone benzoate (0.100 g) from a preceding batch. The crystallization progresses at 77° C. and after 15 min, the reaction is cooled at a ramp of −10° C/h. When the reaction reaches 61° C., both the stirring and the cooling are stopped and the reaction is allowed to cool to rt. After standing overnight, stirring is resumed and the product is collected by filtration. The filter cake is washed with a solvent mixture prepared from toluene (3 L) and cyclohexane (1.5 L). After drying partially by suction, the product is transferred to a drying oven where it is dried at 40° C. affording [4-(5-aminomethyl-2-fluorophenyl)piperidine-1-yl][7-fluoro-1-(2-methoxyethyl)-4-trifluoromethoxy-1H-indol-3-yl]methanone benzoate as a colorless solid: 1408.8 g (86%), mp=156-159° C. Elemental analysis: Calculated for C₂₅H₂₆F₅N₃O₃·C₇H₆O₂: C, 60.66; H, 5.09; N, 6.63. Found: C, 60.44; H, 5.01; N, 6.87. Infrared spectral features (cm-1): 1612, 1526, 1511, 1501, 1394, 1362, 1256, 1232, 1211, 1158, 1117, 999, 826.

Scheme 2

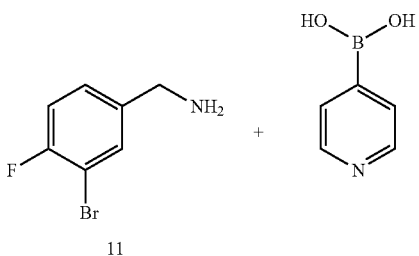 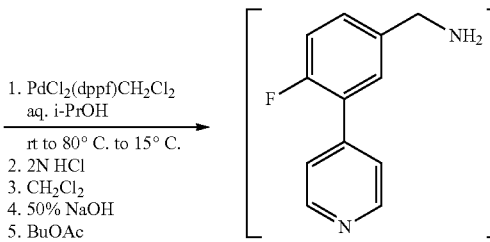

1. PdCl₂(dppf)CH₂Cl₂
   aq. i-PrOH
   rt to 80° C. to 15° C.
2. 2N HCl
3. CH₂Cl₂
4. 50% NaOH
5. BuOAc step 1
6. TFAA, 5° C.
7. 10% Na₂CO₃
8. 5-6N HCl in i-PrOH
9. BuOAc

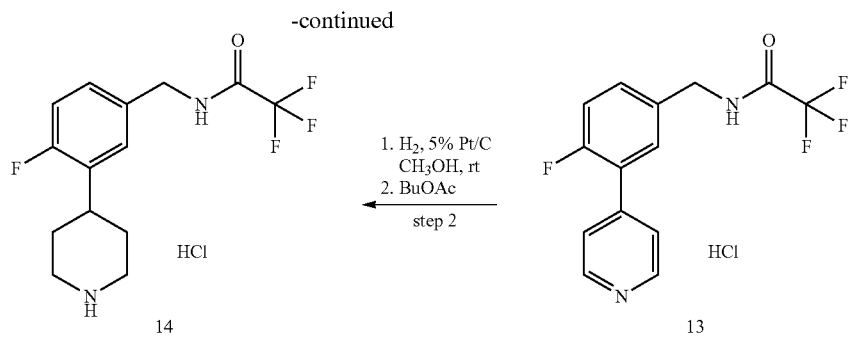

3-Bromo-4-fluorobenzylamine hydrochloride (Wychem) is reacted with pyridine-4-boronic acid (Clariant or Boron Molecular) in an alcoholic solvent with a boiling point of at least that of isopropyl alcohol, such as n-propyl alcohol, n-butyl alcohol and the like; polar aprotic solvent such as dimethylformamide, 1-methyl-2-pyrrolidone, dimethylsulfoxide, and the like etheral solvent such as 2-methyltetrahydrofuran, dimethoxyethane, and the like. Compound 12 and compound 13 in mixture of any of the above mentioned solvents and water in the presence of a suitable catalyst such as 1,1'-bis(diphenylphosphino)ferrocene-palladium(II) dichloride dichloromethane complex ($PdCl_2dppf-CH_2Cl_2$), $Pd(PPh_3)_4$, $PdCl_2(PPh_3)_2$, $Pd(dtbpf)Cl_2$, and the like with sufficient heating from about 70° C. to the temperature of the boiling point of the Suzuki coupling reaction mixture provides the pyridine.

This pyridine is converted to the trifluoroacetamide compound 2,2,2-trifluoro-N-(4-fluoro-3-pyridin-4-yl-benzyl)-acetamide hydrochloride under trifluoroacetylating conditions using a suitable trifluoroacetylating agent such as trifluoroacetic anhydride, trifluoroacetyl fluoride, pentafluorophenyl trifluoroacetate and the like, in a trifluoroacetylating solvent such as an ester solvent such as ethyl acetate, isopropyl acetate, or the like; an aromatic hydrocarbon solvent such as toluene, or the like; a chlorinated hydrocarbon solvent such as methylene chloride, 1,2-dichloroethane, or the like, at a trifluoroacetylation reaction temperature of about −20 to about 30° C., followed by treatment with hydrochloric acid.

2,2,2-Trifluoro-N-(4-fluoro-3-pyridin-4-yl-benzyl)-acetamide hydrochloride is reduced to under hydrogenation conditions to compound 14 by treatment with hydrogen in the presence of a hydrogenation catalyst means $PtO_2$, Pd/C, $Pd(OH)_2$, Rh/C and the like, with or without added inorganic acid such as HCl and the like, or organic acid such as acetic acid and the like, in a hydrogenation reaction solvent such as an alcohol solvent such as ethanol, isopropyl alcohol and the like; or acetic acid; or a mixture of an alcohol solvent or acetic acid and water, at hydrogenation reaction temperature of from about 10 to about 60° C., and hydrogenation pressure of from about 20 to about 1000 psi.

The compound of the present invention is basic, and such compound is useful in the form of the free base or in the form of a pharmaceutically acceptable acid addition salt thereof.

Acid addition salts may be a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compound is preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochloride and hydrobromide, sulfates, phosphates, nitrates, sulfamates, acetates, citrates, lactates, tartrates, malonates, oxalates, salicylates, propionates, succinates, fumarates, maleates, methylene-bis-b-hydroxynaphthoates, benzoates, tosylates, gentisates, isethionates, di-p-toluoyltartrates, methanesulfonates, ethanesulfonates, benzenesulfonates, p-toluenesulfonates, cyclohexylsulfamates and quinates. A more particular salt is salt of the compound of formula I is the hydrochloride salt. Another particular salt of the present invention is the fumarate of the compound of formula I. A preferred pharmaceutically acceptable salt of the present invention is the benzoate of the compound of formula I.

As well as being useful in itself as an active compound, salts of the compound of the invention are useful for the purposes of purification of the compound, for example by exploitation of the solubility differences between the salts and the parent compound, side products and/or starting materials by techniques well known to those skilled in the art.

According to a further feature of the invention, the acid addition salt of the compound of this invention may be prepared by reaction of the free base with the appropriate acid, by the application or adaptation of known methods. For example, the acid addition salts of the compound of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compound of this invention can be regenerated from the salts by the application or adaptation of known methods. For example, the parent compound of the invention can be regenerated from their acid addition salts by treatment with an alkali, e.g. aqueous sodium bicarbonate solution or aqueous ammonia solution.

The starting materials and intermediates may be prepared by the application or adaptation of known methods, for example methods as described in the Reference Examples or their obvious chemical equivalents.

The present invention is also directed to some intermediates in the above scheme 1 and, as such, the processes described herein for their preparation constitute further features of the present invention.

EXAMPLES

The present invention may be better understood by reference to the following non-limiting Examples, which are provided as exemplary of the invention. The following Examples are presented in order to more fully illustrate particular embodiments of the invention. They should in no way be construed, however, as limiting the broad scope of the invention. The Reference Example below is provided to disclose how to make an intermediate used for making the compound of formula I.

In the nuclear magnetic resonance spectra (NMR), reported infra, the chemical shifts are expressed in ppm relative to tetramethylsilane. Abbreviations have the following significances: br=broad, dd=double doublet, s=singlet; m=multiplet.

Reference Example 1

Step A: Preparation of 2,2,2-Trifluoro-N-(4-fluoro-3-pyridin-4-yl-benzyl)-acetamide hydrochloride (13)

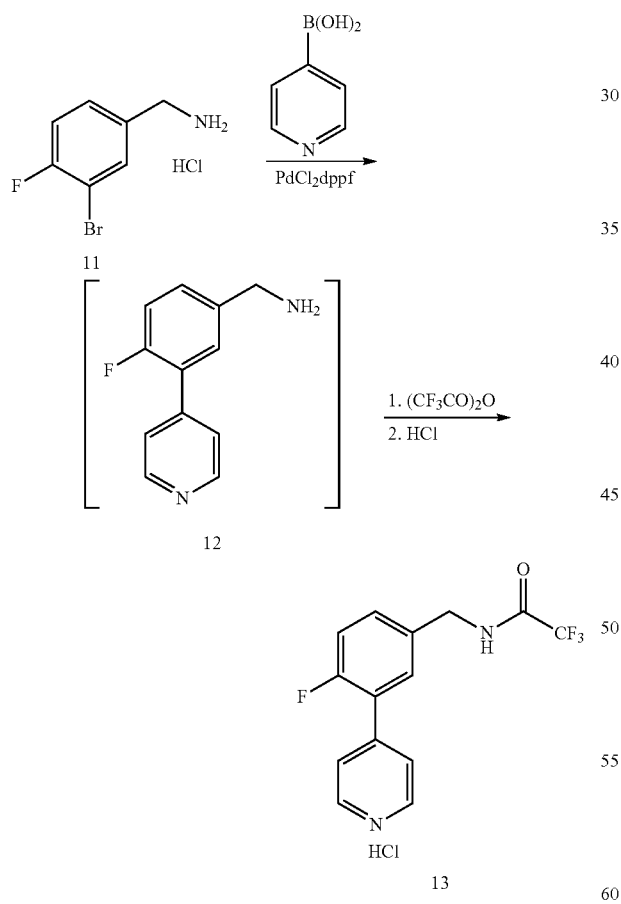

A flask is charged with NaHCO$_3$ (126 g, 1.5 mol), 3-bromo-4-fluorobenzylamine hydrochloride (11, 120 g, 0.5 mole) and pyridine-4-boronic acid (13, 67.6 g, 0.55 mmol) and iPrOH (750 mL) and water (375 mL) at rt. The suspension is degassed with N$_2$ for 1 h at 10° C. Into the mixture is added 1,1'-bis(diphenylphosphino)ferrocene-palladium(II)dichloride dichloromethane complex (PdCl$_2$dppf-CH$_2$Cl$_2$, 16.4 g, 20 mmol). The reaction mixture is heated to 80° C. while some part is distilled off until the internal temperature reaches 80° C., and stirred for 10 h. After the reaction is completed (HPLC analysis), the mixture is cooled to rt, and aqueous 2 N HCl (750 mL) is added, and stirred for 0.5 h. The solution is washed with DCM (750 mL and 500 mL). To the aqueous phase is charged 50% aqueous NaOH (100 mL) to adjust pH>13. After adding n-BuOAc (2 L), activated carbon (50 g) is added into the organic layer. This mixture is filtered through a pad of Celite (50 g). Azeotropic distillation is performed. After adding an additional n-BuOAc (1 L), the reaction is cooled to 5° C. TFAA (157 g, 0.6 mol) is slowly added into the solution at 5° C. After the reaction is completed (HPLC analysis), the reaction mixture is washed with aqueous 10% Na$_2$CO$_3$ (1 L). A solution of 5-6 N HCl in iPrOH (120 mL) is introduced into the crude organic layer at 10° C. Additional n-BuOAc (1 L) is then added, the suspension is left overnight at rt. The resultant solid is filtered at 10° C., and dried in oven at 50° C. to give 124 g (75%) of compound 15 as white solid: mp=220° C. Anal. Calcd for C$_{14}$H$_{10}$F$_4$N$_2$O—HCl: C, 50.24; H, 3.31; N, 8.37. Found: C, 50.16; H, 3.08; N, 8.38. MS (ESI) m/z 299 (M+H). $^1$H NMR (300 MHz, D$_2$O) δ 8.70 (d, J=6.9 Hz, 2 H), 8.14 (d, J=6.9 Hz, 2H), 7.56-7.20 (m, 3H), 4.51 (s, 2H).

Step B: Preparation of 2,2,2-trifluoro-N-(4-fluoro-3-piperidin-4-yl-benzyl)-acetamide hydrochloride (14)

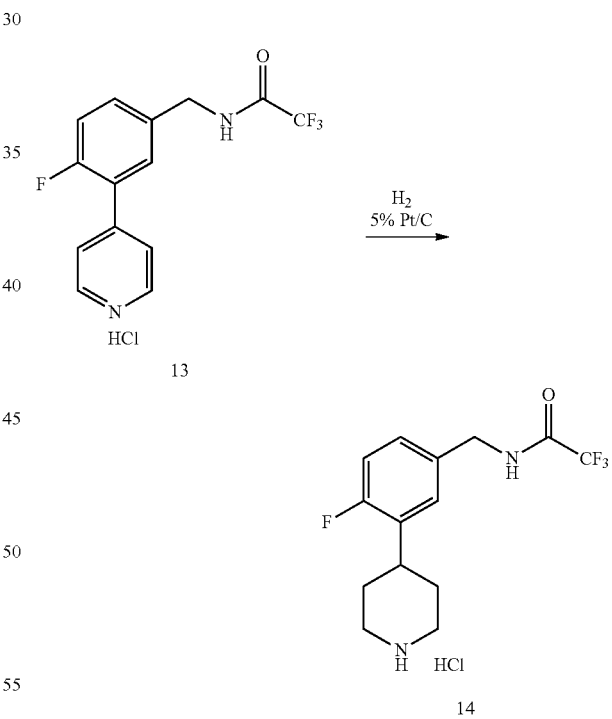

A Parr flask is charged with compound 13 (123 g, 0.37 mol) and MeOH (740 mL) at rt, then 5% Pt/C (36.9 g, 30 w/w%) is added. The reaction flask is placed in a Parr hydrogenation system and charged with H$_2$ at 50-60 psi. The mixture is shaken for >48 h while charging H$_2$ until the pressure reached a steady state (H$_2$ was refilled to 50-60 psi every 2-3 hours during day time while 10-20 psi is observed without any further refill after overnight). When HPLC analysis shows completion of the reaction, the reaction mixture is filtered through a pad of Celite. The filtrate is distilled at 40-50° C.

while adding n-BuOAc (1.25 L). After completion of distillation of MeOH, additional n-BuOAc (1 L) is added. The resultant suspension is allowed to cool to rt overnight. The suspension is cooled to 10° C., filtered, and dried in oven at 50° C. to give 112 g (89%) of compound 14 as white solid: mp=134° C. Anal. Calcd for $C_{14}H_{10}F_4N_2O$—HCl: C, 50.24; H, 3.31; N, 8.37. Found: C, 50.16; H, 3.08; N, 8.38. MS (ESI) m/z 305.4 (M+H). $^1$H NMR (300 MHz, $D_2O$) δ 7.16-6.98 (m, 3H), 4.34 (s, 2H), 3.42 (d, J=12.9 Hz, 2H), 3.14-2.99 (m, 3H), 1.98-1.81 (m, 4H).

Reference Example 2

Step A: Preparation of (2-Fluoro-5-trifluoromethoxy-phenyl)-carbamic acid ethyl ester (2)

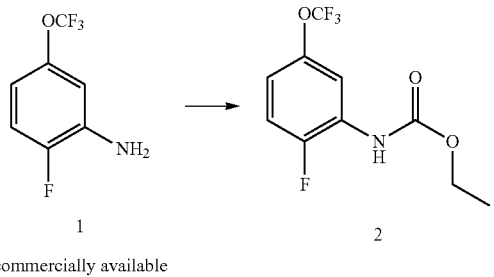

commercially available

To a solution of 1 (50.72 g, 0.26 mol) and pyridine (27.3 mL, 0.34 mol) in THF (500 mL) at 0° C. is added ethyl chloroformate (32.2 mL, 0.39 mol) dropwise over a 30 min period. After 1 h, both LC/MS and TLC indicate that the reaction is completed. The reaction mixture is partitioned between $H_2O$ and EtOAc. The two layers are separated, and the organic layer is washed with 1 M HCl, $H_2O$, and brine, dried over $MgSO_4$, filtered, and concentrated in vacuo. The crude material is purified on silica gel with heptane/EtOAc (95/5 to 70/30) as eluant to give 69.23 g (99%) of the product 2 as a clear colorless liquid. $^1$H NMR ($CDCl_3$) δ 8.11 (br s, 1H), 7.07 (dd, J=9.1, 9.3 Hz, 1H), 7.00-6.80 (m, 2H), 4.27 (q, J=7.1 Hz, 2H), 1.33 (t, J=7.1 Hz, 3H); $^{19}$F NMR ($CDCl_3$) δ 57.84 (s, 3F), −134.01 (br s, 1F); MS 309 (M+CH3CN+1, 100%), 268 (M+1).

Step B: Preparation of (6-Fluoro-2-iodo-3-trifluoromethoxy-phenyl)-carbamic acid ethyl ester (3)

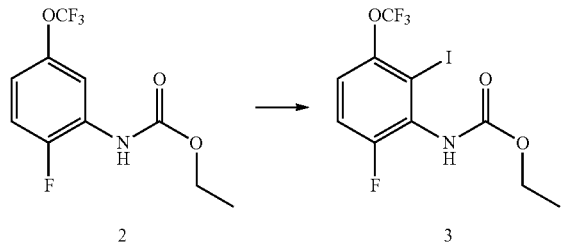

To a solution of 2 (31.34 g, 117.2 mmol) in THF (180 mL) at −78° C. is added sec-BuLi (1.4 M in cyclohexane, 200 mL, 280 mmol) dropwise over a 1 h period. After 20 min, a solution of $I_2$ (44.6 g, 175.8 mmol) in THF (150 mL) is added dropwise over a 30 min period. This mixture is then stirred at −78° C. for 30 min. Saturated $NH_4Cl$ is added, and the cooling bath is removed. The reaction mixture is partitioned between $H_2O$ and EtOAc. The two layers are separated, and the organic layer is washed with 10% $Na_2SO_3$, $H_2O$, and brine, dried over $MgSO_4$, filtered, and concentrated in vacuo. The residue is suspended in DCM (50 mL), and heptane (300 mL) is added. The white powder 3 (18.1 g, 39%) from the resulting suspension is collected by suction filtration and air-dried. The filtrate is concentrated in vacuo, and the residue is suspended in heptane (200 mL). Another batch of 3 (3.8 g, 8%) is collected by suction filtration and air-dried. Additional product can be obtained by purifying the filtrate via silica gel chromatography. $^1$H NMR ($CDCl_3$) δ 7.30-17.10 (m, 2H), 6.16 (br s, 1H), 4.26 (q, J=7.1 Hz, 2H), 1.32 (t, J=7.1 Hz, 3H); $^{19}$F NMR ($CDCl_3$) δ −56.90 (s, 3F), −114.35 (d, J=8.5 Hz, 1F); MS 394 (M+1, 100%), 374, 364, 321, 267.

Step C: Preparation of (6-Fluoro-3-trifluoromethoxy-2-trimethylsilanylethynyl-phenyl)-carbamic acid ethyl ester (4)

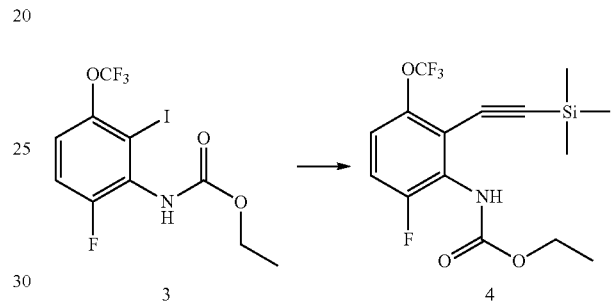

A mixture of 3 (18.1 g, 45.9 mmol), $Et_3N$ (12.8 mL, 91.9 mmol), $Pd(PPh)_2Cl_2$ (1.6 g, 5% mol), CuI (0.7 g, 8% mol), and TMS-acetylene (19.6 mL, 137.8 mmol) in degassed THF (180 mL) is heated at 60° C. overnight. The mixture is cooled to rt, and then partitioned between $H_2O$ and EtOAc. This mixture is filtered through Celite to remove the insoluble material. The two layers of the filtrate are separated, and the organic layer is washed $H_2O$ and brine, dried over $MgSO_4$, filtered, and concentrated in vacuo. The crude material is purified on silica gel with heptane/EtOAc as eluant to give 15.6 g (93%) of the product 4 as beige solid. $^1$H NMR ($CDCl_3$) δ 7.15-7.00 (m, 2H), 6.41 (br s, 1H), 4.26 (q, J=7.1 Hz, 2H), 1.31 (t, J=7.1 Hz, 3H), 0.27 (s, 9H); $^{19}$F NMR ($CDCl_3$) δ −57.59 (s, 3F), −118.15 (s, 1F); MS 364 (M+1, 100%).

Step D: Preparation of 7-Fluoro-4-trifluoromethoxy-1H-indole (5)

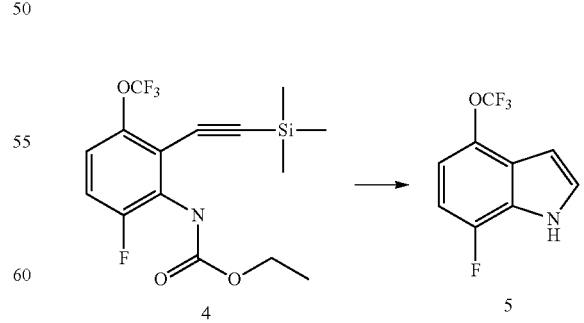

A mixture of 4 (28.9 g, 79.6 mmol) and KOH (35.7 g, 636.7 mmol) in degassed t-BuOH (300 mL) is heated at 70° C. overnight. LC/MS indicates the reaction is completed. The mixture is cooled to rt, and then partitioned between $H_2O$ and Et₂O. The two layers are separated, and the aqueous layer was extracted with Et₂O (2×). The combined organic layers are washed with H₂O and brine, dried over MgSO₄, filtered, and concentrated in vacuo. The crude material is purified on silica gel with heptane/EtOAc (100/0 to 60/40) as eluant to give 16 g (91%) of 5 as a yellow liquid. ¹H NMR (CDCl₃) δ 8.47 (br s, 1H), 7.35-7.20 (m, 1H), 6.95-6.80 (m, 2H), 6.68 (d, J=2.5 Hz, 1H); ¹⁹F NMR (CDCl3) δ −57.63 (s, 3F), −136.10 (d, J=8.5 Hz, 1F); MS 220 (M+1, 100%), 200.

Step E: Preparation of 7-Fluoro-1-(2-methoxy-ethyl)-4-trifluoromethoxy-1H-indole (6)

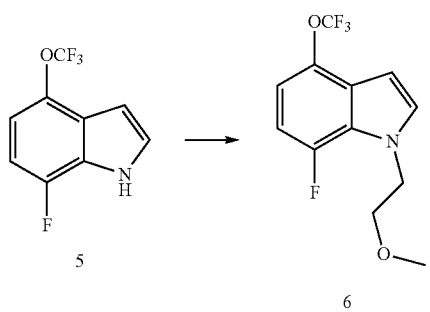

A mixture of 5 (16 g, 72.8 mmol) and powder KOH (20.4 g, 364.2 mmol) in DMSO (150 mL) is stirred at rt for 10 min. 2-Methoxyethyl bromide (10.3 mL, 109.2 mmol) is added. This mixture is stirred at rt overnight. LC/MS indicates the reaction is completed. The mixture is partitioned between H₂O and Et₂O. The two layers are separated, and the aqueous layer is extracted with Et₂O (2×). The combined organic layers are washed with H₂O and brine, dried over MgSO₄, filtered, and concentrated in vacuo. The crude material is purified on silica gel with heptane/EtOAc (100/0 to 50/50) as eluant to give 19.3 g (95%) of 6 as a yellow liquid. ¹H NMR (CDCl₃) δ 7.15 (d, J=2.1 Hz, 1H), 6.90-6.75 (m, 2H), 6.56 (t, J=2.5 Hz, 1H), 3.72 (t, J=5.2 Hz, 2H), 3.72 (t, J=5.2 Hz, 2H), 3.31 (s, 3H); ¹⁹F NMR (CDCl₃) δ −57.54 (s, 3F), −137.00 (d, J=11.3 Hz, 1F); MS 278 (M+1, 100%).

Step F: Preparation of 2,2,2-Trifluoro-1-[7-fluoro-1-(2-methoxy-ethyl)-4-trifluoromethoxy-1H-indol-3-yl]-ethanone (7)

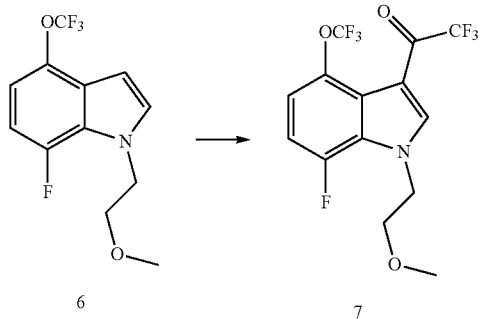

To a mixture of 6 (19.3 g, 69.7 mmol) in DMF (135 mL) is added TFAA (26.2 mL, 188.2 mmol). This mixture is heated at 40° C. overnight. TLC indicates the reaction is completed. The mixture is cooled to rt, and then partitioned between H₂O and Et₂O. The two layers are separated, and the organic layer is washed with saturated NaHCO₃ (2×), H₂O and brine, dried over MgSO₄, filtered, and concentrated in vacuo. The crude material is purified on silica gel with heptane/EtOAc (100/0 to 50/50) as eluant to give 23.4 g (89%) of 7 as a slightly green solid. ¹H NMR (CDCl₃) δ 8.03 (d, J=1.4 Hz, 1H), 7.20-6.95 (m, 2H), 4.54 (t, J=4.9 Hz, 2H), 3.76 (t, J=4.8 Hz, 2H), 3.33 (s, 3H); ¹⁹F NMR (CDCl₃) δ −57.74 (s, 3F), −71.10 (s, 3F), −134.95 (d, J=11.5 Hz, 1F); MS 374 (M+1, 100%).

Step G: Preparation of 7-Fluoro-1-(2-methoxy-ethyl)-4-trifluoromethoxy-1H-indole-3-carboxylic acid (8)

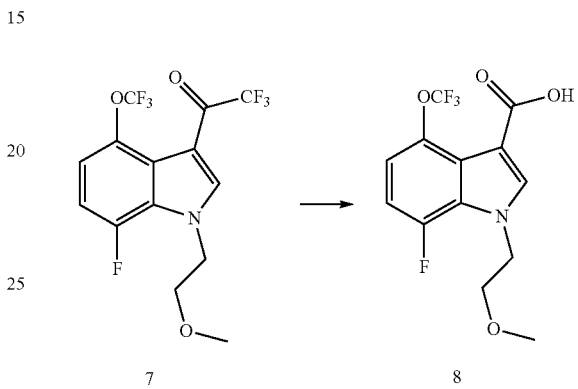

A mixture of 7 (23.4 g, 62.6 mmol) in MeOH (100 mL) and 5 M NaOH (100 mL) is heated at 80° C. overnight. LC/MS indicates that the reaction is complete. The reaction mixture is cooled to rt, and then concentrated in vacuo to remove most of the MeOH. The residue is dissolved in H₂O, and then washed with Et₂O once. The aqueous layer is slowly acidified to pH ~2 with conc. HCl. The acidified suspension is extracted with Et₂O, and the organic extract is washed with H₂O and brine, dried over MgSO₄, filtered, and concentrated in vacuo. The residue is suspended in DCM/heptane (10/90). The white powder 8 (19.4 g, 96%) in the suspension is collected by suction filtration and air-dried. ¹H NMR (CDCl₃) δ 8.02 (s, 1H), 7.15-7.05 (m, 1H), 7.00-6.90 (m, 1H), 4.49 (t, J=5.0 Hz, 2H), 3.75 (t, J=4.9 Hz, 2H), 3.33 (s, 3H); ¹⁹F NMR (CDCl₃) δ −57.74 (s, 3F), −135.65 (d, J=11.3 Hz, 1F); MS 363 (M+CH₃CN+1), 322 (M+1, 100%).

Step H: Preparation of 2,2,2-Trifluoro-N-(4-fluoro-3-{1-[7-fluoro-1-(2-methoxy-ethyl)-4-trifluoromethoxy-1H-indole-3-carbonyl]-piperidin-4-yl}-benzyl)-acetamide (9)

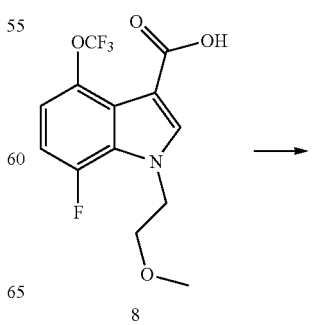

-continued

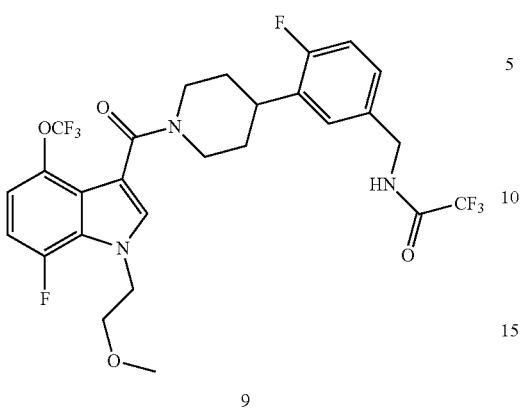

9

A mixture of 8 (19.1 g, 59.6 mmol), Et₃N (24.8 mL, 177.9 mmol), 2,2,2-trifluoro-N-(4-fluoro-3-piperidin-4-yl-benzyl)-acetamide hydrochloride (11, 26.4 g, 77.5 mmol) (14), and EDCI (17.1 g, 89.3 mmol) in CH₂Cl₂ is stirred at rt overnight. Both TLC and LC/MS indicate that the reaction is completed. The mixture is partitioned between H₂O and CH₂Cl₂. The two layers are separated, and the organic layer is washed with brine, dried over MgSO₄, filtered, and concentrated in vacuo. The crude material is purified on silica gel with heptane/EtOAc (40/60 to 0/100) as eluant to give 9 (36 g, 99%) as a white foam. $^1$H NMR (CDCl₃) δ 7.37 (s, 1H), 7.20-7.10 (m, 2H), 7.10-6.85 (m, 4H), 4.95 (br s, 1H), 4.60-4.35 (m, 4H), 3.90 (br s, 1H), 3.73 (t, J=5.0 Hz, 2H), 3.32 (s, 3H), 3.25-2.70 (m, 3H), 2.05-1.50 (m, 4H); $^{19}$F NMR (CDCl₃) δ −57.54 (s, 3F), −75.39 (s, 3F), −119.31 (s, 1F), −134.96 (d, J=11.3 Hz, 1F); MS 608 (M+1, 100%).

Step I: Preparation of [4-(5-Aminomethyl-2-fluorophenyl)-piperidin-1-yl]-[7-fluoro-1-(2-methoxyethyl)-4-trifluoromethoxy-1H-indol-3-yl]methanone hydrochloride salt (10)

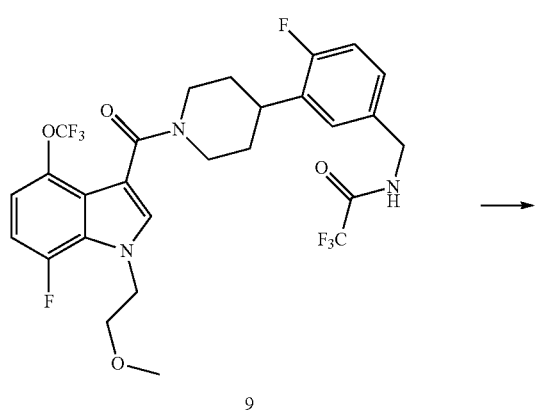

9

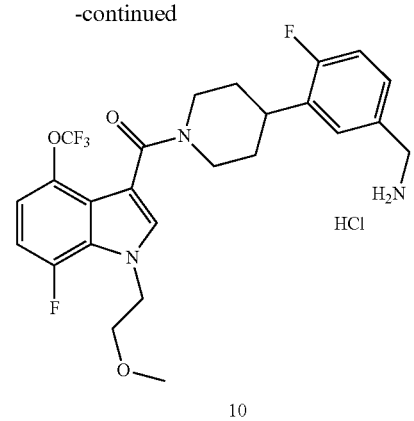

10

To a mixture of 9 (36 g, 59.3 mmol) in MeOH (400 mL) is added aqueous K₂CO₃ (65.5 g, 474 mmol, dissolved in 120 mL H₂O). This mixture is stirred at rt overnight. LC/MS indicates the reaction is completed. The reaction mixture is concentrated in vacuo to remove most of the methanol. The residue is partitioned between H₂O and EtOAc. The two layers are separated, and the organic layer is washed with H₂O and brine, dried over MgSO₄, filtered, and concentrated in vacuo to yield 27.5 g (90%) of 10 as a clear colorless sticky gum.
$^1$H NMR (CDCl₃) δ 7.42 (s, 1H), 7.25-7.10 (m, 2H), 7.05-6.85 (m, 3H), 4.92 (br s, 1H), 4.46 (t, J=5.2 Hz, 2H), 3.86 (br s, 3H), 3.74 (t, J=5.1 Hz, 2H), 3.32 (s, 3H), 3.30-2.75 (m, 3H), 2.24 (br s, 2H), 2.05-1.55 (m, 4H); $^{19}$F NMR (CDCl₃) δ −57.52 (s, 3F), −121.64 (s, 1F), −136.03 (d, J=11.3 Hz, 1F); MS 512 (M+1, 100%).

To a solution of the above material (2.856 g, 5.59 mmol) in Et₂O (30 mL) is added 2 N HCl/Et₂O (3 mL, 6 mmol) dropwise. A solid precipitate forms and the ethereal solution is decanted off. The solid is washed with additional Et₂O then decanted off. The remaining pale yellow solid is dissolved in warm MeOH (10 mL) then Et₂O (50 mL) is added until the solution is slightly cloudy. After ca. 2 hrs solid precipitate appears. Additional Et₂O (5-10 mL) is added and then the suspension is placed in the fridge overnight. A white crystalline product (2.475 g, 4.52 mmol) is collected and dried under high vacuum for 4 hrs.
$^1$H NMR (DMSO-d₆) δ 8.32 (br s, 2H), 7.71 (s, 1H), 7.43 (d, 1H, J=7.2 Hz), 7.36 (m, 1H), 7.26-7.20 (m, 1H), 7.12-7.08 (m, 2H), 4.49 (t, J=5.1 Hz, 2H), 4.00 (s, 2H), 3.71 (t, J=5.1 Hz, 2H), 3.32 (s, 3H), 3.21-3.07 (m, 3H), 2.99 (br s, 2H), 1.80-1.62 (m, 4H); $^{19}$F NMR (DMSO-d₆) δ −56.79 (s, 3F), −119.34 (s, 1F), −134.53 (d, J=9.6 Hz, 1F); MS 512 (M+1, 100%). CHN:

Theoretical: C, 53.06%, H, 5.16%, N, 7.42% (calc'd as 1.0 H₂O). Found: C, 53.03%, H, 4.82%, N, 7.22; Cl, 6.64%.

Reference Example 3

Benzoate Salt of the Compound of Formula I

A 20-L glass-jacketed reactor already containing a toluene solution assumed to contain [4-(5-aminomethyl-2-fluorophenyl)piperidine-1-yl][7-fluoro-1-(2-methoxyethyl)-4-trifluoromethoxy-1H-indol-3-yl]methanone (1320 g, 2.58 mol) is stirred and heated to 61° C. Benzoic acid (316 g, 2.58 mol) is added and, after all the benzoic acid has dissolved, cyclohexane (6.04 L) is added. The reaction is heated to 77° C. where it is seeded with [4-(5-aminomethyl-2-fluorophenyl)piperidine-1-yl][7-fluoro-1-(2-methoxyethyl)-4-trifluoromethoxy-1H-indol-3-yl]methanone benzoate (0.100 g) from a preceding batch. The crystallization progresses at 77° C. and after 15 min, the reaction is cooled at a ramp of –10° C./h. When the reaction reaches 61° C., both the stirring and the cooling are stopped and the reaction is allowed to cool to rt. After standing overnight, stirring is resumed and the product is collected by filtration. The filter cake is washed with a solvent mixture prepared from toluene (3 L) and cyclohexane (1.5 L). After drying partially by suction, the product is transferred to a drying oven where it is dried at 40° C. affording [4-(5-aminomethyl-2-fluorophenyl)piperidine-1-yl][7-fluoro-1-(2-methoxyethyl)-4-trifluoromethoxy-1H-indol-3-yl]methanone benzoate as a colorless solid: 1408.8 g (86%), mp=156-159° C.

Reference Example 4

Besylate Salt of the Compound of Formula I

[4-(5-Aminomethyl-2-fluorophenyl)piperidine-1-yl][7-fluoro-1-(2-methoxyethyl)-4-trifluoromethoxy-1H-indol-3-yl]methanone Benzenesulfonate A solution of benzenesulfonic acid monohydrate (698 mg, 3.84 mmol) in acetonitrile (12 mL) was added drop-wise to a stirred suspension of [4-(5-aminomethyl-2-fluorophenyl)piperidine-1-yl][7-fluoro-1-(2-methoxyethyl)-4-trifluoromethoxy-1H-indol-3-yl]methanone (2.0 g, 3.91 mmol) in acetonitrile (5 mL). The benzenesulfonate salt began to crystallize from the mixture as the last of the free base dissolved. After 2 h, the product was collected by filtration and washed with acetonitrile. The filter cake was allowed to dry overnight. The solids were broken up and dried in a vacuum oven @43-44° C. at 6.8-7.3" of Hg with a nitrogen bleed for 7.5 h to give [4-(5-aminomethyl-2-fluorophenyl)piperidine-1-yl][7-fluoro-1-(2-methoxyethyl)-4-trifluoromethoxy-1H-indol-3-yl]methanone benzenesulfonate as a colorless solid: 2.27 g 1 (86.7%), mp=215-218° C. Anal. Calculated. For $C_{25}H_{26}F_5N_3O_3 \cdot C_6H_6O_3S$: C, 55.60; H, 4.82; N, 6.27. Found: C, 55.65; H, 4.65; N, 6.27. Karl Fischer: <0.10. Infrared spectral features (cm-1): 1587, 1545, 1445, 1210, 1167, 1125, 1036, 1018.

Reference Example 5

Sesquifumarate Salt of the Compound of Formula I

[4-(5-Aminomethyl-2-fluorophenyl)piperidine-1-yl][7-fluoro-1-(2-methoxyethyl)-4-trifluoromethoxy-1H-indol-3-yl]methanone Sesquifumarate Monohydrate A round-bottom flask was charged with [4-(5-aminomethyl-2-fluorophenyl)-piperidine-1-yl][7-fluoro-1-(2-methoxyethyl)-4-trifluoromethoxy-1H-indol-3-yl]methanone (10.4 g, 20.4 mmol) and fumaric acid (4.74 g, 40.7 mmol). Isopropanol (IPA, 62 mL) was added and the resulting mixture was heated on a steam bath. Most of the material dissolved, before crystallization of the salt occurred. While being heated on a steam bath, additional IPA was added in 30 mL portions. Complete solution was attained after the addition of a total of 152 mL of IPA. The resulting solution was filtered and the filtrate was allowed to cool to rt. The filtrate was cooled further in an ice bath for 1.5 h, before the product was collected by filtration. The collected product was washed with cold IPA (50 mL), dried partially by suction and transferred to a drying oven where it was dried at 45° C. After drying overnight, the desired product was isolated as colorless solid: 11.8 g (84%). IR (cm$^{-1}$): 3122-2700, 2920, 2824, 1698, 1584, 1512, 1443, 1397-1368, 1293-1217, 822, 794, 639. $^1$H NMR (300 MHz, DMSO-d6): δ 10.07 (br, 3H), 7.71 (s, 1H), 7.43 (dd, J=2.4, 7.1, 1H), 7.36 (ddd, J=2.4, 4.9, 8.4, 1H), 7.19 (d, J=8.4, 10.7, 1H), 7.10 (d, J=8.7, 11.7, 1H), 7.05 (ddd, J=1.4, 3.3, 8.7, 1H), 6.50 (s, 3H), 4.69 (br, 1H), 4.48 (t, J=5.3, 2H), 3.97 (s, 2H), 3.69 (t, J=5.4, 2H), 3.24 (s, 3H), 3.08 (dddd, J=3.5, 3.5, 12.1, 12.1, 1H), 2.91 (br, 2H), 1.75 (br, 2H), 1.63 (br, 2H). Anal. Calcd for $C_{25}H_{26}F_5N_3O_3 \cdot 1.5C_4H_4O_4$: C, 54.31; H, 4.70; N, 6.13. Found: C, 54.30; H, 4.62; N, 6.04. MS (ESI) m/z 512.2 (M+H).

Reference Example 6

Tosylate Salt of the Compound of Formula I

[4-(5-Aminomethyl-2-fluoro-phenyl)-piperidin-1-yl]-[7-fluoro-1-(2-methoxy-ethyl)-4-trifluoromethoxy-1H-indol-3-yl]-methanone p-toluenesulfonic Acid To a mixture of [4-(5-aminomethyl-2-fluoro-phenyl)-piperidin-1-yl]-[7-fluoro-1-(2-methoxy-ethyl)-4-trifluoromethoxy-1H-indol-3-yl]-methanone (488 mg, 0.95 mmol) in acetonitrile (3 mL) is added a solution of p-toluenesulfonic acid monohydrate (181 mg, 0.95 mmol) in acetonitrile (3 mL). This mixture is stored in a freezer overnight. The resulting beige crystal is collected by suction filtration, washed with toluene, and dried in vacuo at 50° C. overnight. The yield is 453 mg (69%). $^1$H NMR (DMSO-d6) δ 8.08 (bs, 3H), 7.70 (s, 1H), 7.80-6.95 (m, 9H), 5.00-4.30 (m, 3H), 4.20-3.90 (m, 2H), 3.80-3.60 (m, 3H), 3.23 (s, 3H), 3.25-2.80 (m, 3H), 2.28 (s, 3H), 1.95-1.45 (m, 4H); $^{19}$F NMR (DMSO-d6) δ –55.61 (s, 3F), –118.98 (s, 1F), –134.33 (d, J=9.3 Hz, 1F); LC 2.627 min; MS 512 (M+1, 100%). Mp 219° C. Infrared spectral features (cm-1): 1583, 1548, 1511, 1501, 1250, 1200, 1169, 1123, 1115.

Reference Example 7

Sulfuric Acid Salt of the Compound of Formula I

[4-(5-aminomethyl-2-fluoro-phenyl)-piperidin-1-yl]-[7-fluoro-1-(2-methoxy-ethyl)-4-trifluoromethoxy-1H-indol-3-yl]-methanone (423 mg, 0.827 mmol) was weighed in a 20 ml glass vial. To this solid was added a solution of sulfuric acid (1.0 N reagent, 1.5 equivalents, 1.30 mmol, 2.60 ml) and 1.7 ml water. After 2 hours stirring at room temperature, crystalline product precipitated. After filtration and drying, the solid was found to be amorphous. When treated with a few drops of water, the amorphous solid returned to a crystalline form. Mp 62° C. Infrared spectral features (cm-1): 1574, 1545, 1511, 1483, 1362, 1267, 1219, 1212, 1162, 1096, 1051.

Reference Example 8

Citric Acid Salt of the Compound of Formula I

[4-(5-aminomethyl-2-fluoro-phenyl)-piperidin-1-yl]-[7-fluoro-1-(2-methoxy-ethyl)-4-trifluoromethoxy-1H-indol-3-yl]-methanone (265 mg, 0.52 mmol) was weighed in a 20 ml glass vial. To this was added a solution of citric acid in 2:1 (v/v) acetonitrile/water (3.30 ml of 0.158 mmol/ml citric acid). All solid dissolved rapidly giving a clear solution which was allowed to stand 1 hour at room temperature. Solution is evaporated under a stream of nitrogen gas, then dried in vacuo at room temperature. The solid was recrystallized in hot acetonitrile with a minimal quantity of water added to give a clear solution. Upon cooling, the solution deposited the product as very long fibrous particles which transformed to a plate habit after standing at room temperature. Mp 112° C. Infrared spectral features (cm-1): 1721, 1590, 1553, 1369, 1245, 1174, 1155, 1119.

Reference Example 9

Methanesulfonic Acid Salt of the Compound of Formula I

[4-(5-aminomethyl-2-fluoro-phenyl)-piperidin-1-yl]-[7-fluoro-1-(2-methoxy-ethyl)-4-trifluoromethoxy-1H-indol-3-yl]-methanone (0.250 g, 0.489 mmol) was weighed in a 20 ml glass vial. Methanesulfonic acid in water (0.98 ml of a 0.50 mmol/ml solution) was added and the mixture was heated with stirring to ~60C. Not all solid dissolved, and an additional 25 µL of methanesulfonic acid solution was added to give a clear solution. After stirring at room temperature for an hour, the solution was evaporated in vacuo on a rotary evaporator to give a very viscous oil. The oil was recrystallized forming square plates in acetonitrile. Infrared spectral features (cm-1): 1596, 1540, 1214, 1159, 1112, 1040, 1020.

Reference Example 10

Tartaric Acid Salt of the Compound of Formula I

[4-(5-aminomethyl-2-fluoro-phenyl)-piperidin-1-yl]-[7-fluoro-1-(2-methoxy-ethyl)-4-trifluoromethoxy-1H-indol-3-yl]-methanone (0.250 g, 0.554 mmol) was weighed in a 20 ml glass vial. A solution of L-(+)-tartaric acid at 2.66 mmol/ml in 5:1 (v/v) acetonitrile/water was prepared, and 0.2084 ml of this solution was added to the weighed solid with stirring and heating to ~60° C. giving a clear solution. The solution was then evaporated in vacuo on a rotary evaporator leaving a glassy solid which was recrystallized in hot isopropyl acetate to which a minimum amount of isopropanol was added to give a clear solution. Upon cooling the crystalline product was isolated by filtration and dried in vacuo at room temperature.

Reference Example 11

Phosphate Salt of the Compound of Formula I

[4-(5-aminomethyl-2-fluoro-phenyl)-piperidin-1-yl]-[7-fluoro-1-(2-methoxy-ethyl)-4-trifluoromethoxy-1H-indol-3-yl]-methanone (133.9 mg, 0.262 mmol), phosphoric acid solution (1 mmole/mL in isopropanol, 1.1 equivalents) was added. The mixture was dissolved in 500 µL isopropanol at room temperature with stirring using a magnetic stirrer. The material was evaporated to dryness at room temperature, with no crystalline material isolated. The material was redissolved in 500 µL acetone, 500 µL ethyl acetate, and 1 mL heptane. The material separated as an oil. The mixture was evaporated to dryness under a nitrogen stream. Once dry, ethyl acetate (500 µL) and toluene (500 µL) were added, where the material separated as an oil. The mixture was allowed to evaporate to dryness overnight at room temperature. Methyl isobutyl ketone (1mL) and toluene (500 µL) were added to dissolve material. Mixture was allowed to evaporate at room temperature overnight. Crystals appeared and were harvested by vacuum filtration at room temperature. Material was dried in vacuum oven (~300 mbar) overnight at room temperature.

Reference Example 12

Glutamate Salt of the Compound of Formula I

[4-(5-aminomethyl-2-fluoro-phenyl)-piperidin-1-yl]-[7-fluoro-1-(2-methoxy-ethyl)-4-trifluoromethoxy-1H-indol-3-yl]-methanone (138.8 mg, 0.271 mmol), glutamic acid solution (162.4 mg/20 ml, in water, 1.1 equivalents) were added. Methanol (2 mL) was added to dissolve material. The mixture was allowed to evaporate overnight at room temperature where a white amorphous material precipitated. To the material, isopropanol (600 µL) was added. Crystals appeared and were harvested by vacuum filtration at room temperature. Material was dried in vacuum oven (~300 mbar) overnight at room temperature.

Reference Example 13

Crystalline Form A of the Benzoate of the Compound of Formula I

Sample Preparation: Material was prepared as in the reference example 3 above. A suspension of the benzoate salt was prepared as 50 mg/mL free base equivalent in nanopure water, which was 63.6 mg salt in 1 mL water. Sample was stirred at 500 rpm overnight and allowed to stand for 4 hours before it was centrifuged (total 29 hours as suspension). It was centrifuged at 13000 rpm for 8 minutes and the collected solid was analyzed by XRPD (x-ray power diffraction) as wet sample and evaluated by microscope. The wet solid was then air dried at ambient room temperature overnight to be analyzed as the dry sample by XRPD and thermal analysis. The as is drug substance is compared as the initial material. The XRPD of free base drug substance was also used as the comparison. The benzoate appeared to be a variable hydrate, with the XRPD displaying the same peaks for different amounts of water.
Instrument Parameter
XRPD Method
Siemens Model D5000 with Cu anticathode
Program: 1.0 Sec. dql
Range: 2° to 40°. 2-θ Scale
Step size: 0.02°
Atmosphere: Ambient conditions of temperature and humidity.
Standard top load and low volume cavity specimen mounts were used
DSC-TGA:
TA Instruments Model Q-600 Simultaneous DSC-TGA
Purge Gas: Helium at 100 mL/min
Temperature Program: 10° C./min linear heating rate
Sample Prep: Approximately 3-5 mg of the powder was transferred to an open Aluminum pan and loaded into the TGA. An empty Aluminum pan was used as a reference.
Result:
XRPD and thermal analyses were carried out on wet and dry samples. XRPD of the wet sample showed some shifting and elevation of baseline. However, upon drying (overnight), XRPD showed improved resolution of peaks comparable to the initial material. Thermal analysis of the dry sample showed the same TGA profile as the initial. Based on XRPD and thermal analysis, no free base or conversions to hydrate form were noted. The free base XRPD is provided in FIG. 1 shows the XRPD results for crystalline form A of the benzoate of the compound of formula I. This figure displays relative intensity (%) versus angle (2 theta) for the sample. Peaks were shown at the following angles: 7.75, 10.13, 17.03, 17.16, 17.99, 18.39, 20.51, 21.33, 21.88, 23.19, 23.43, and 27.59.

Figure 2:
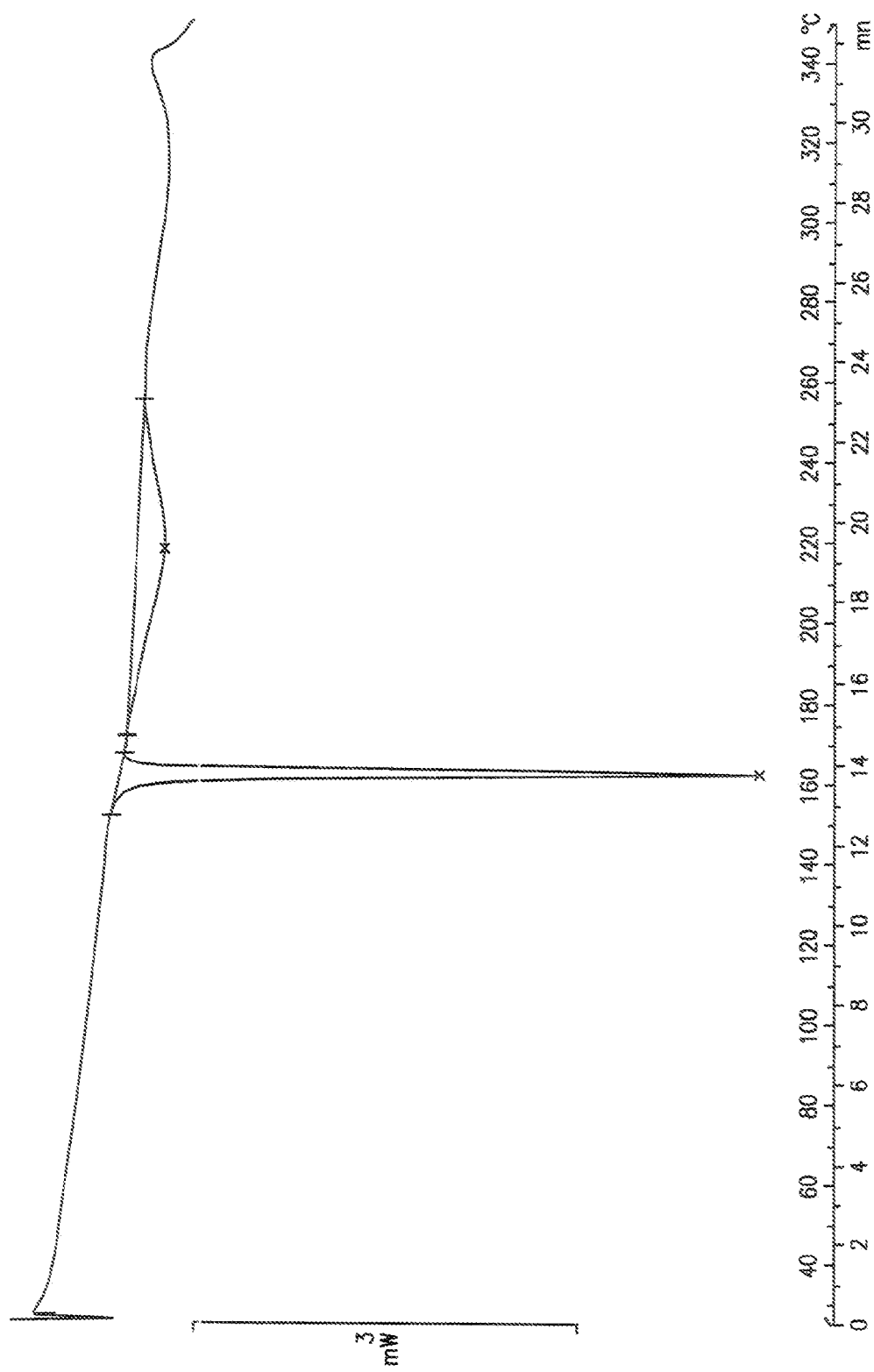
FIG. 2 shows the DSC results for crystalline form A of the benzoate of the compound of formula I.

FIG. 2 shows the DSC results for crystalline form A of the benzoate of the compound of formula I. This figure shows onset of melting at 160.29° C. and melting of the form at 162° C.

Biological Activity

The properties of the compound of the present invention are demonstrated by: 1) its β-Tryptase Inhibitory Potency ($IC_{50}$ and $K_i$ values).

In Vitro Test Procedure

As all the actions of tryptase, as described in the background section, are dependent on its catalytic activity, then compounds that inhibit its catalytic activity will potentially inhibit the actions of tryptase Inhibition of this catalytic activity may be measured by the in vitro enzyme assay and the cellular assay.

Tryptase inhibition activity is confirmed using either isolated human lung tryptase or recombinant human β tryptase expressed in yeast cells. Essentially equivalent results are obtained using isolated native enzyme or the expressed enzyme. The assay procedure employs a 96 well microplate (Costar 3590) using L-pyroglutamyl-L-prolyl-L-arginine-para-nitroanilide (S2366: Quadratech) as substrate (essentially as described by McEuen et. al. Biochem Pharm, 1996, 52, pages 331-340). Assays are performed at room temperature using 0.5 mM substrate ($2 \times K_m$) in 50 mM Tris (pH 8.2), 100 mM NaCl, 0.05% Tween 20, 50 µg/mL heparin, and the microplate is read on a microplate reader (Beckman Biomek Plate reader) at 405 nm wavelength.

Protocol ($IC_{50}$ and $K_i$ Determination)

The protocol is essentially the same as above except that the compound is added in duplicates at the following final concentrations: 0.01, 0.03, 0.1, 0.3, 1, 3, 10 µM (All dilutions carried out manually). For every assay, whether single point or $IC_{50}$ determination, a standard compound is used to derive $IC_{50}$ for comparison. From the $IC_{50}$ value, the $K_i$ can be calculated using the following formula: $K_i = IC_{50}/(1+[\text{Substrate}]/K_m)$.

The β-Tryptase inhibitory potency for the compound of formula I is $K_i$ value of 26±5 nM.

Protocol for Antigen-Induced Airway Hyperactivity Assay

Antigen sensitization and challenge: Male Hartley guinea pigs (225-250 g) were sensitized with ovalbumin (0.5 ml of 1% solution, i.p. and s.c.) on day 1 (Aug. 25, 2008). On day 4 (Aug. 28, 2008), animals received a booster injection (i.p.) of 0.5 ml of 1% ovalbumin. On day 21 (Sep. 16, 2008), animals were orally dosed (2 ml/kg) with either vehicle (0.5% methylcellulose/0.2% Tween 80) or compound(s) 24 hours prior to antigen challenge. Thirty minutes before antigen challenge the animals were also injected with mepyramine (10 mg/kg, i.p.) to prevent anaphylactic collapse. Animals were then exposed for 20 min to an aerosol of 1% ovalbumin using a DeVilbiss Ultraneb nebulizer. Negative control animals were not challenged. Sensitizing solution: One gram (1 g) of albumin from chicken egg white (Sigma A55031G; lot#087K7004) was added to 100 ml of saline and allowed to go into solution.

Airway resistance measurement: Eighteen to twenty four hours after challenge, animals were anesthetized, (0.5 ml dose (i.m.) of cocktail containing ketamine (62 mg/kg), xylazine (30 mg/kg) and Promace (1.5 mg/kg)), surgically prepared and then placed in a whole body plethysmograph. Animals were connected to Ugo-Basile ventilators delivering a tidal volume of 1 ml/100 g at a rate of 50 breaths/minute via a tracheal cannula. The jugular vein is also cannulated for histamine challenge. A-water filled esophageal cannula was placed such that transpulmonary pressure could be recorded. Transpulmonary pressure was measured as the difference between the tracheal and esophageal cannulas using a differential pressure transducer. The volume, airflow, and transpulmonary pressure signals are monitored using a pulmonary analysis system (Buxco XA software) and used to calculate pulmonary resistance (cmH2O/ml/s) and dynamic compliance (ml/cmH20). Airway resistance and dynamic compliance are computed on a breath-by-breath basis. Histamine is administered intravenously and reactivity to increasing concentrations (1-20 µg/kg) assessed.

Results with this assay for the fumarate salt of the compound of Formula I are shown in the following tables. This assay is related to the effectiveness of compounds for potentially treating asthma. The fumarate salt of the compound of Formula I showed dose-related inhibition of antigen-induced airway hyperreactivity when dosed 24 hours prior to allergen challenge, as indicated by these tables.

TABLE 1

Inhibition of Antigen-induced Airway Hyperactivity in Guinea Pig: Airway Resistance Fumarate Salt:

| Dose of Compound (mg/kg) | Increase in Airway Resistance (Area Under Curve) |
|---|---|
| Saline | 3490 +/− 506 |
| OVA (no treatment) | 12586 +/− 1488 |
| 0.01 Fumarate Salt | 9647 +/− 818 |
| 0.03 Fumarate Salt | 8103 +/− 745 |
| 0.1 Fumarate Salt | 6623 +/− 511 |

TABLE 2

Antigen-induced Airway Hyperactivity in Guinea Pig: Dynamic Lung Compliance in Guinea Pig Fumarate Salt:

| Dose of Compound (mg/kg) | Dynamic Lung Compliance (Area Under Curve) |
|---|---|
| Saline | −799 +/− 46 |
| OVA (no treatment) | −1386 +/− 22 |
| 0.01 Fumarate Salt | −1218 +/− 47 |
| 0.03 Fumarate Salt | −1156 +/− 40 |
| 0.1 Fumarate Salt | −1004 +/− 43 |

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:
1. A compound of formula I:

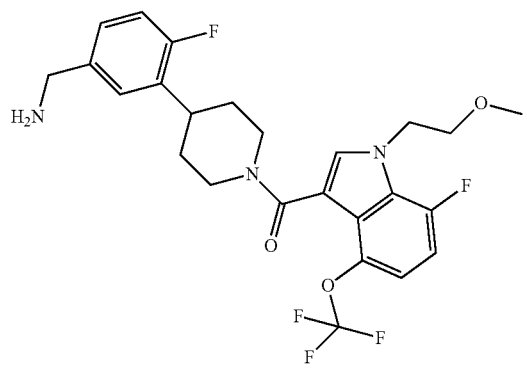

(I)

or a pharmaceutically acceptable salt thereof.

2. The compound of claim 1 as a pharmaceutically acceptable salt selected from: hydrochloride, fumarate, besylate, tosylate, sulfate, citrate, methanesulfonate, tartrate, phosphate, glutamate and benzoate.

3. The compound according to claim 2, wherein the salt is benzoate.

4. A crystalline form A of the compound according to claim 3, wherein the crystalline form has XRPD peaks at at least five of the following 2 theta angles: 7.75; 10.13; 17.03; 17.16; 18.39; 21.33; and 21.88.

5. A crystalline form of the compound according to claim 3, wherein the crystalline form melts at 162 degrees Celsius.

6. A method for treating a patient suffering from a physiological condition selected from the group consisting of inflammatory disease, a disease of joint cartilage destruction, inflammatory bowel disease, asthma, interstitial lung disease, fibrosis, chronic obstructive pulmonary disease, pulmonary fibrosis, myocardial fibrosis, and neurofibroma, comprising administering to the patient a therapeutically effective amount of the compound according to claim 1.

7. The method of claim 6, wherein the physiological condition is COPD.

8. An intermediate compound having a formula selected from the group consisting of:

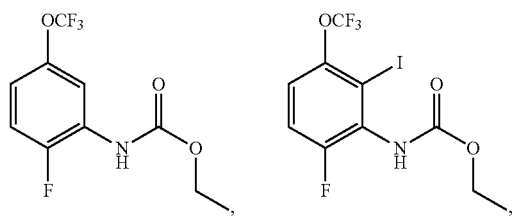

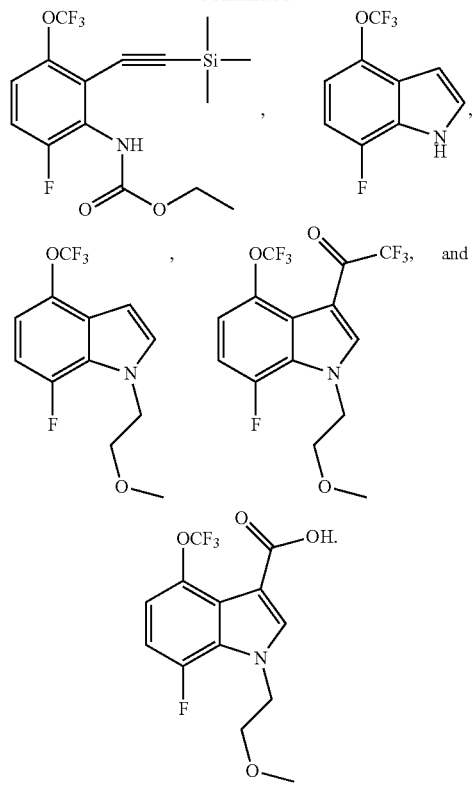

9. A compound having the formula:

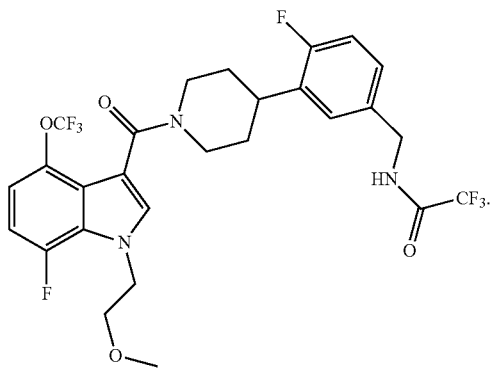

* * * * *